US009622746B2

(12) United States Patent
Simms et al.

(10) Patent No.: US 9,622,746 B2
(45) Date of Patent: Apr. 18, 2017

(54) DISTAL TIP FEATURES FOR END EFFECTOR OF SURGICAL INSTRUMENT

(71) Applicant: Ethicon Endo-Surgery, Inc., Cincinnati, OH (US)

(72) Inventors: Robert J. Simms, Liberty Township, OH (US); Douglas B. Hoffman, Harrison, OH (US); Rebecca J. Gettinger, Loveland, OH (US); Timothy S. Bedard, Sewickley, PA (US); Dean L. Garner, Cincinnati, OH (US); Glen A. Armstrong, Liberty Township, OH (US); Janna B. Volz, Fort Thomas, KY (US)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 759 days.

(21) Appl. No.: 13/780,171

(22) Filed: Feb. 28, 2013

(65) Prior Publication Data

US 2014/0239043 A1 Aug. 28, 2014

(51) Int. Cl.
*A61B 17/068* (2006.01)
*A61B 17/072* (2006.01)
(Continued)

(52) U.S. Cl.
CPC ............... *A61B 17/07207* (2013.01); *A61B 2017/00398* (2013.01); *A61B 2017/00734* (2013.01);
(Continued)

(58) Field of Classification Search
CPC .... A61B 2019/481; A61B 2017/00738; A61B 2017/07257; A61B 2017/07271; A61B 2017/320048; A61B 2017/320044
(Continued)

(56) References Cited

U.S. PATENT DOCUMENTS

| 4,805,823 | A | | 2/1989 | Rothfuss | |
| 5,403,312 | A | * | 4/1995 | Yates | ............... A61B 17/07207 606/142 |

(Continued)

FOREIGN PATENT DOCUMENTS

| EP | 1 943 961 A2 | 7/2008 |
| EP | 2 353 518 A1 | 8/2011 |
| WO | WO 2004/096057 A2 | 11/2004 |

OTHER PUBLICATIONS

U.S. Appl. No. 13/780,067, filed Feb. 28, 2013.
(Continued)

*Primary Examiner* — Robert Long
*Assistant Examiner* — Xavier A Madison
(74) *Attorney, Agent, or Firm* — Frost Brown Todd LLC

(57) ABSTRACT

An apparatus comprises a body, a shaft, and an end effector that is operable to compress, staple, and cut tissue. The end effector comprises and anvil and a cartridge. A longitudinal axis intersects the distal tip of the anvil when the anvil is in a closed position. The cartridge defines a sight line extending along a distal surface of the cartridge from a first side of the cartridge toward the anvil. The first side of the cartridge is opposite to the anvil. The distal surface of the cartridge is neither parallel to nor perpendicular to the longitudinal axis. The sight line intersects the longitudinal axis near the distal tip when the anvil is in the closed position. A segment of the sight line and a segment the longitudinal axis define an angle θ. The angle θ is larger than 90°.

20 Claims, 20 Drawing Sheets

(51) Int. Cl.
*A61B 17/00* (2006.01)
*A61B 90/00* (2016.01)

(52) U.S. Cl.
CPC .............. *A61B 2017/00738* (2013.01); *A61B 2017/00858* (2013.01); *A61B 2017/07257* (2013.01); *A61B 2017/07271* (2013.01); *A61B 2090/08021* (2016.02)

(58) Field of Classification Search
USPC ........................................................ 606/190
See application file for complete search history.

(56) References Cited

U.S. PATENT DOCUMENTS

| | | | |
|---|---|---|---|
| 5,415,334 A | 5/1995 | Williamson, IV et al. | |
| 5,465,895 A | 11/1995 | Knodel et al. | |
| 5,597,107 A | 1/1997 | Knodel et al. | |
| 5,632,432 A | 5/1997 | Schulze et al. | |
| 5,662,258 A | 9/1997 | Knodel et al. | |
| 5,662,667 A | 9/1997 | Knodel | |
| 5,673,840 A | 10/1997 | Schulze et al. | |
| 5,704,534 A | 1/1998 | Huitema et al. | |
| 5,735,445 A | 4/1998 | Vidal et al. | |
| 5,792,135 A | 8/1998 | Madhani et al. | |
| 5,814,055 A | 9/1998 | Knodel et al. | |
| 5,817,084 A | 10/1998 | Jensen | |
| 5,878,193 A | 3/1999 | Wang et al. | |
| 6,231,565 B1 | 5/2001 | Tovey et al. | |
| 6,241,740 B1 * | 6/2001 | Davis ................. A61B 17/1227 606/139 | |
| 6,364,888 B1 | 4/2002 | Niemeyer et al. | |
| 6,783,524 B2 | 8/2004 | Anderson et al. | |
| 6,905,057 B2 | 6/2005 | Swayze et al. | |
| 6,959,852 B2 | 11/2005 | Shelton, IV et al. | |
| 6,978,921 B2 | 12/2005 | Shelton, IV et al. | |
| 7,000,818 B2 | 2/2006 | Shelton, IV et al. | |
| 7,044,352 B2 | 5/2006 | Shelton, IV et al. | |
| 7,083,075 B2 | 8/2006 | Swayze et al. | |
| 7,097,650 B2 | 8/2006 | Weller et al. | |
| 7,143,923 B2 | 12/2006 | Shelton, IV et al. | |
| 7,143,926 B2 | 12/2006 | Shelton, IV et al. | |
| 7,303,108 B2 | 12/2007 | Shelton, IV | |
| 7,364,061 B2 | 4/2008 | Swayze et al. | |
| 7,367,485 B2 | 5/2008 | Shelton, IV et al. | |
| 7,380,695 B2 | 6/2008 | Doll et al. | |
| 7,380,696 B2 | 6/2008 | Shelton, IV et al. | |
| 7,404,508 B2 | 7/2008 | Smith et al. | |
| 7,434,715 B2 | 10/2008 | Shelton, IV et al. | |
| 7,524,320 B2 | 4/2009 | Tierney et al. | |
| 7,644,848 B2 | 1/2010 | Swayze et al. | |
| 7,691,098 B2 | 4/2010 | Wallace et al. | |
| 7,721,930 B2 | 5/2010 | McKenna et al. | |
| 7,743,960 B2 | 6/2010 | Whitman et al. | |
| 7,806,891 B2 | 10/2010 | Nowlin et al. | |
| 8,210,411 B2 | 7/2012 | Yates et al. | |
| 8,408,439 B2 | 4/2013 | Huang et al. | |
| 8,453,914 B2 | 6/2013 | Laurent et al. | |
| 8,479,969 B2 | 7/2013 | Shelton, IV et al. | |
| 8,573,461 B2 | 11/2013 | Shelton, IV et al. | |
| 8,573,465 B2 | 11/2013 | Shelton, IV et al. | |
| 8,602,288 B2 | 12/2013 | Shelton, IV et al. | |
| 8,616,431 B2 | 12/2013 | Timm et al. | |
| 8,684,253 B2 * | 4/2014 | Giordano ........ A61B 17/00234 227/180.1 | |
| 2006/0180634 A1 | 8/2006 | Shelton, IV et al. | |
| 2007/0010838 A1 | 1/2007 | Shelton, IV et al. | |
| 2007/0084897 A1 | 4/2007 | Shelton, IV et al. | |
| 2007/0175955 A1 | 8/2007 | Shelton, IV et al. | |
| 2008/0269793 A1 * | 10/2008 | Scirica ............. A61B 17/07207 606/190 | |
| 2010/0094315 A1 * | 4/2010 | Beardsley ........ A61B 17/07207 606/143 | |
| 2011/0186614 A1 * | 8/2011 | Kasvikis .......... A61B 17/07207 227/175.2 | |
| 2011/0226837 A1 * | 9/2011 | Baxter, III ......... A61B 17/0644 227/175.1 | |
| 2012/0080498 A1 | 4/2012 | Shelton et al. | |
| 2012/0138660 A1 | 6/2012 | Shelton, IV et al. | |
| 2012/0199630 A1 | 8/2012 | Shelton, IV et al. | |
| 2012/0199632 A1 | 8/2012 | Spivey et al. | |
| 2012/0203247 A1 | 8/2012 | Shelton, IV et al. | |
| 2013/0012957 A1 | 1/2013 | Shelton, IV et al. | |

OTHER PUBLICATIONS

U.S. Appl. No. 13/780,082, filed Feb. 28, 2013.
U.S. Appl. No. 13/780,106, filed Feb. 28, 2013.
U.S. Appl. No. 13/780,120, filed Feb. 28, 2013.
U.S. Appl. No. 13/780,379, filed Feb. 28, 2013.
U.S. Appl. No. 13/780,402, filed Feb. 28, 2013.
U.S. Appl. No. 13/780,417, filed Feb. 28, 2013.
Partial European Search Report dated May 23, 2014 for Application No. EP 14157372.5, 6 pgs.
European Search Report and Written Opinion dated Sep. 8, 2014 for Application No. EP 14157372.5, 12 pgs.
International Search Report dated Sep. 26, 2014 for Application No. PCT/US2014/017298, 9 pgs.
International Preliminary Report on Patentability and Written Opinion dated Sep. 1, 2015 for Application No. PCT/US2014/017298, 11 pgs.

* cited by examiner

DISTAL TIP FEATURES FOR END EFFECTOR OF SURGICAL INSTRUMENT

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pub. No. 2010/0264193, entitled "Surgical Stapling Instrument with An Articulatable End Effector," published Oct. 21, 2010, issued as U.S. Pat. No. 8,408,439 on Apr. 2, 2013; and U.S. Pub. No. 2012/0239012, entitled "Motor-Driven Surgical Cutting Instrument with Electric Actuator Directional Control Assembly," published Sep. 20, 2012, issued as U.S. Pat. No. 8,453,914 on Jun. 4, 2013. The disclosure of each of the above-cited U.S. Patents and U.S. Patent Publications is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
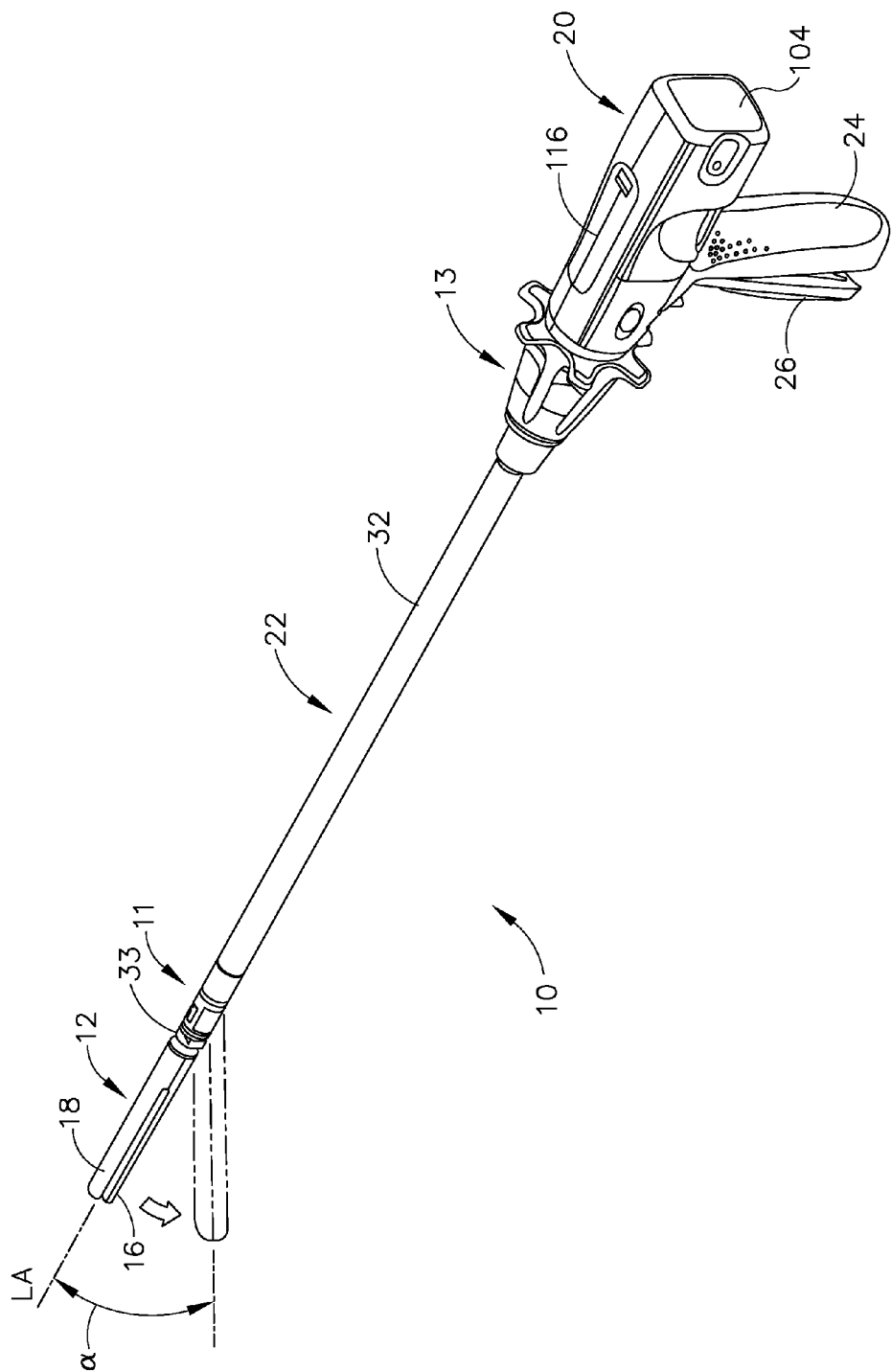
FIG. 1 depicts a perspective view of an exemplary articulating surgical stapling instrument.
Figure 2:
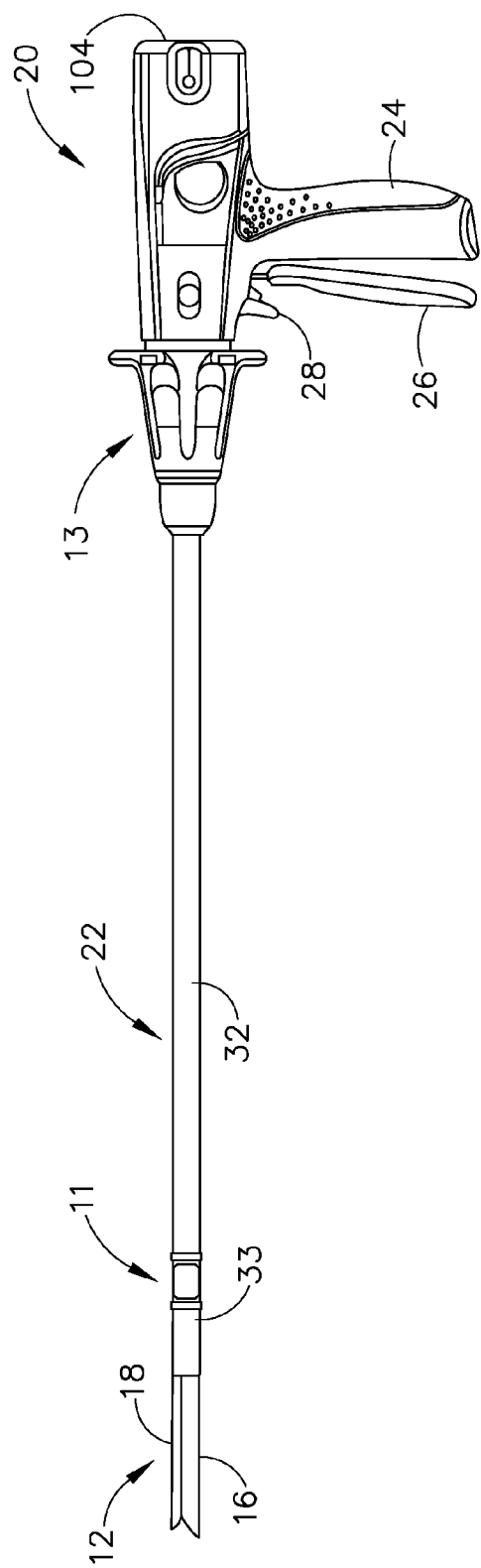
FIG. 2 depicts a side elevational view of the instrument of FIG. 1.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Stapler

FIGS. 1-7 depict an exemplary surgical stapling and severing instrument (10) that is sized for insertion, in a nonarticulated state as depicted in FIG. 1, through a trocar cannula to a surgical site in a patient for performing a surgical procedure. By way of example only, such a trocar may be inserted in a patient's abdomen, between two of the patient's ribs, or elsewhere. In some settings, instrument (10) is used without a trocar. For instance, instrument (10) may be inserted directly through a thoracotomy or other type of incision. Instrument (10) of the present example includes a handle portion (20) connected to a shaft (22). Shaft (22) distally terminates in an articulation joint (11), which is further coupled with an end effector (12). It should be understood that terms such as "proximal" and "distal" are used herein with reference to a clinician gripping handle portion (20) of instrument (10). Thus, end effector (12) is distal with respect to the more proximal handle portion (20). It will be further appreciated that for convenience and clarity, spatial terms such as "vertical" and "horizontal" are used herein with respect to the drawings. However, surgical instruments are used in many orientations and positions, and these terms are not intended to be limiting and absolute.

In some versions, shaft (22) is constructed in accordance with at least some of the teachings of U.S. patent application Ser. No. 13/780,402, entitled "Surgical Instrument with Multi-Diameter Shaft," filed on even date herewith, and published on Aug. 28, 2014 as U.S. Pat. Pub. No. 2014/0239038, the disclosure of which is incorporated by reference herein. Other suitable configurations for shaft (22) will be apparent to those of ordinary skill in the art in view of the teachings herein.

Once articulation joint (11) and end effector (12) are inserted through the cannula passageway of a trocar, articulation joint (11) may be remotely articulated, as depicted in phantom in FIG. 1, by an articulation control (13), such that end effector (12) may be deflected from the longitudinal axis (LA) of shaft (22) at a desired angle ($\alpha$). End effector (12) may thereby reach behind an organ or approach tissue from a desired angle or for other reasons. In some versions, articulation joint (11) enables deflection of end effector (12) along a single plane. In some other versions, articulation joint (11) enables deflection of end effector along more than one plane. Articulation joint (11) and articulation control (13) may be configured in accordance with the teachings of any of the numerous references that are cited herein. Alternatively, articulation joint (11) and/or articulation control (13) may have any other suitable configuration. By way of example only, articulation control (13) may instead be configured as a knob that rotates about an axis that is perpendicular to the longitudinal axis (LA) of shaft (22).

In some versions, articulation joint (11) and/or articulation control (13) are/is constructed and operable in accordance with at least some of the teachings of U.S. patent application Ser. No. 13/780,067, entitled "Surgical Instrument End Effector Articulation Drive with Pinion and Opposing Racks," filed on even date herewith (now U.S. Pat. No. 9,186,142, issued on Nov. 17, 2015), the disclosure of which is incorporated by reference herein. Articulation joint (11) may also be constructed and operable in accordance with at least some of the teachings of U.S. patent application Ser. No. 13/780,402, entitled "Surgical Instrument with Multi-Diameter Shaft", published as U.S. Pat. Pub. No. 2014/0239038 on Aug. 28, 2014, the disclosure of which is incorporated by reference herein. Other suitable forms that articulation joint (11) and articulation control (13) may take will be apparent to those of ordinary skill in the art in view of the teachings herein.

End effector (12) of the present example includes a lower jaw (16) and a pivotable anvil (18). In some versions, lower jaw (16) is constructed in accordance with at least some of the teachings of U.S. patent application Ser. No. 13/780,417, entitled "Installation Features for Surgical Instrument End Effector Cartridge," filed on even date herewith, published as U.S. Pat. Pub. No. 2014/0239044 on Aug. 28, 2014, the disclosure of which is incorporated by reference herein. Anvil (18) may be constructed in accordance with at least some of the teachings of U.S. patent application Ser. No. 13/780,106, entitled "Integrated Tissue Positioning and Jaw Alignment Features for Surgical Stapler," filed on even date herewith, published as U.S. Pat. Pub. No. 2014/0239042 on Aug. 28, 2014, the disclosure of which is incorporated by reference herein; at least some of the teachings of U.S. patent application Ser. No. 13/780,120, entitled "Jaw Closure Feature for End Effector of Surgical Instrument," filed on even date herewith, published as U.S. Pat. Pub. No. 2014/0239036 on Aug. 28, 2014, the disclosure of which is incorporated by reference herein; and/or at least some of the teachings of U.S. patent application Ser. No. 13/780,379, entitled "Staple Forming Features for Surgical Stapling Instrument," filed on even date herewith, published as U.S. Pat. Pub. No. 2014/0239037 on Aug. 28, 2014, the disclosure of which is incorporated by reference herein. Other suitable forms that lower jaw (16) and anvil (18) may take will be apparent to those of ordinary skill in the art in view of the teachings herein.

Handle portion (20) includes a pistol grip (24) and a closure trigger (26). Closure trigger (26) is pivotable toward pistol grip (24) to cause clamping, or closing, of the anvil (18) toward lower jaw (16) of end effector (12). Such closing of anvil (18) is provided through a closure tube (32) and a closure ring (33), which both longitudinally translate relative to handle portion (20) in response to pivoting of closure trigger (26) relative to pistol grip (24). Closure tube (32) extends along the length of shaft (22); and closure ring (33) is positioned distal to articulation joint (11). Articulation joint (11) is operable to communicate/transmit longitudinal movement from closure tube (32) to closure ring (33).

Handle portion (20) also includes a firing trigger (28). An elongate member (136) (shown in FIG. 11) longitudinally extends through shaft (22) and communicates a longitudinal firing motion from handle portion (20) to a firing beam (14) in response to actuation of firing trigger (28). This distal translation of firing beam (14) causes the stapling and severing of clamped tissue in end effector (12), as will be described in greater detail below. Thereafter, triggers (26, 28) may be released to release the tissue from end effector (12).

FIGS. 3-6 depict end effector (12) employing an E-beam form of firing beam (14) to perform a number of functions. It should be understood that an E-beam form is just a merely illustrative example. Firing beam (14) may take any other suitable form, including but not limited to non-E-beam forms. As best seen in FIGS. 4A-4B, firing beam (14) includes a transversely oriented upper pin (38), a firing beam cap (44), a transversely oriented middle pin (46), and a distally presented cutting edge (48). Upper pin (38) is positioned and translatable within a longitudinal anvil slot (42) of anvil (18). Firing beam cap (44) slidably engages a lower surface of lower jaw (16) by having firing beam (14) extend through lower jaw slot (45) (shown in FIG. 4B) that is formed through lower jaw (16). Middle pin (46) slidingly engages a top surface of lower jaw (16), cooperating with firing beam cap (44). Thereby, firing beam (14) affirmatively spaces end effector (12) during firing.

Some non-E-beam forms of firing beam (14) may lack upper pin (38), middle pin (46) and/or firing beam cap (44). Some such versions of instrument (10) may simply rely on closure ring (33) or some other feature to pivot anvil (18) to a closed position and hold anvil (18) in the closed position while firing beam (14) advances to the distal position. By way of example only, firing beam (14) and/or associated lockout features may be constructed and operable in accordance with at least some of the teachings of U.S. patent application Ser. No. 13/780,082, entitled "Lockout Feature for Movable Cutting Member of Surgical Instrument," filed on even date herewith, published as U.S. Pat. Pub. No. 2014/0239041 on Aug. 28, 2014, the disclosure of which is incorporated by reference herein. Other suitable forms that firing beam (14) may take will be apparent to those of ordinary skill in the art in view of the teachings herein.

Figure 3:
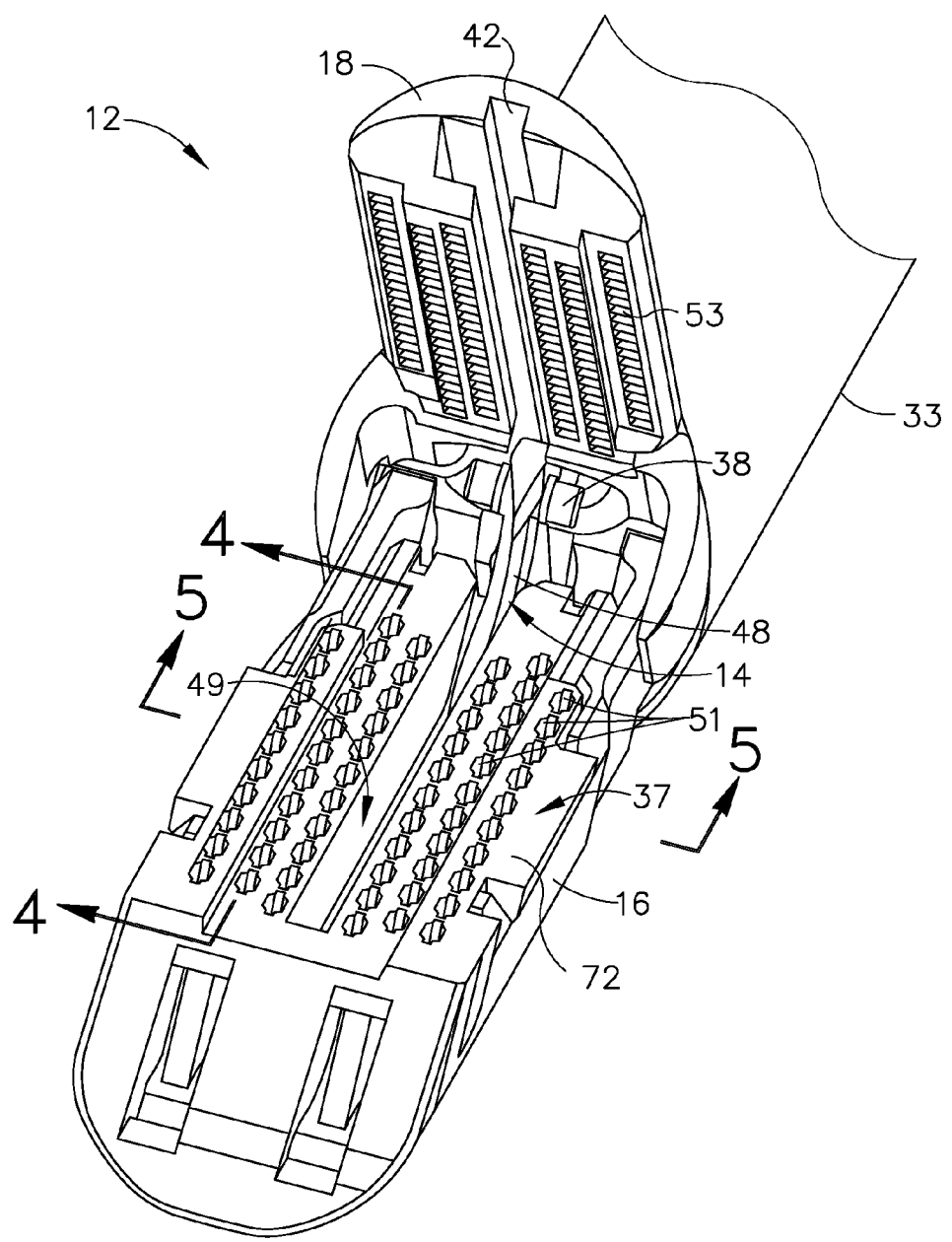
FIG. 3 depicts a perspective view of an opened end effector of the instrument of FIG. 1.
Figure 4A:
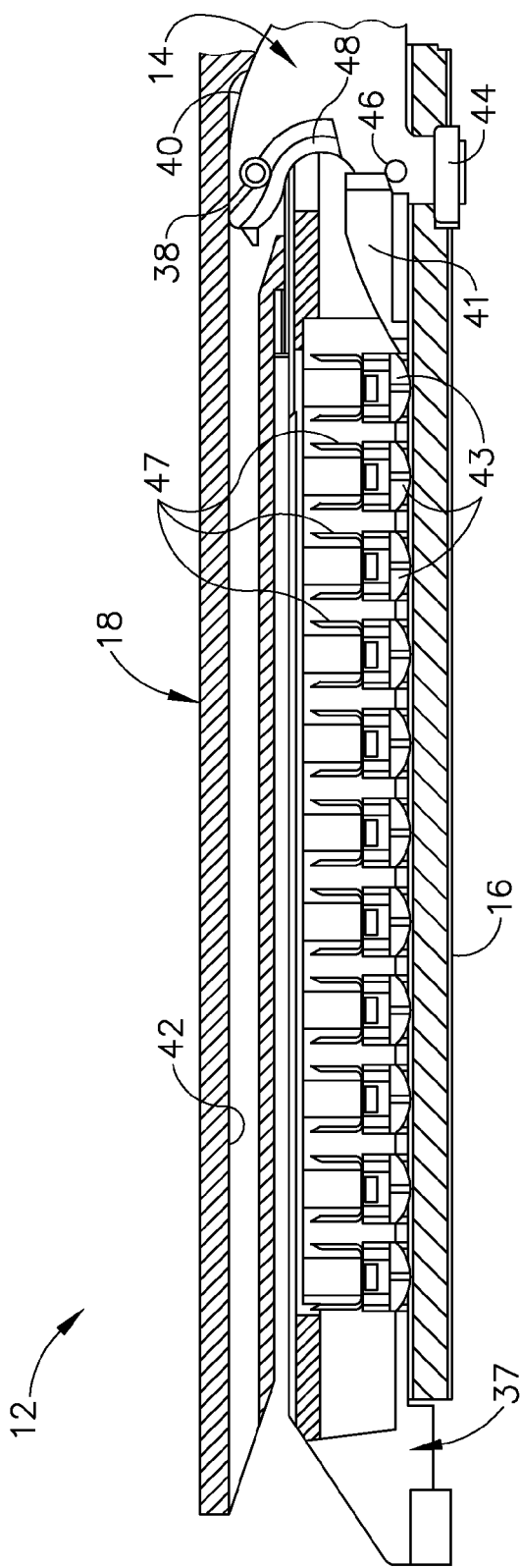
FIG. 4A depicts a side cross-sectional view of the end effector of FIG. 3, taken along line 4-4 of FIG. 3, with the firing beam in a proximal position.
Figure 4B:
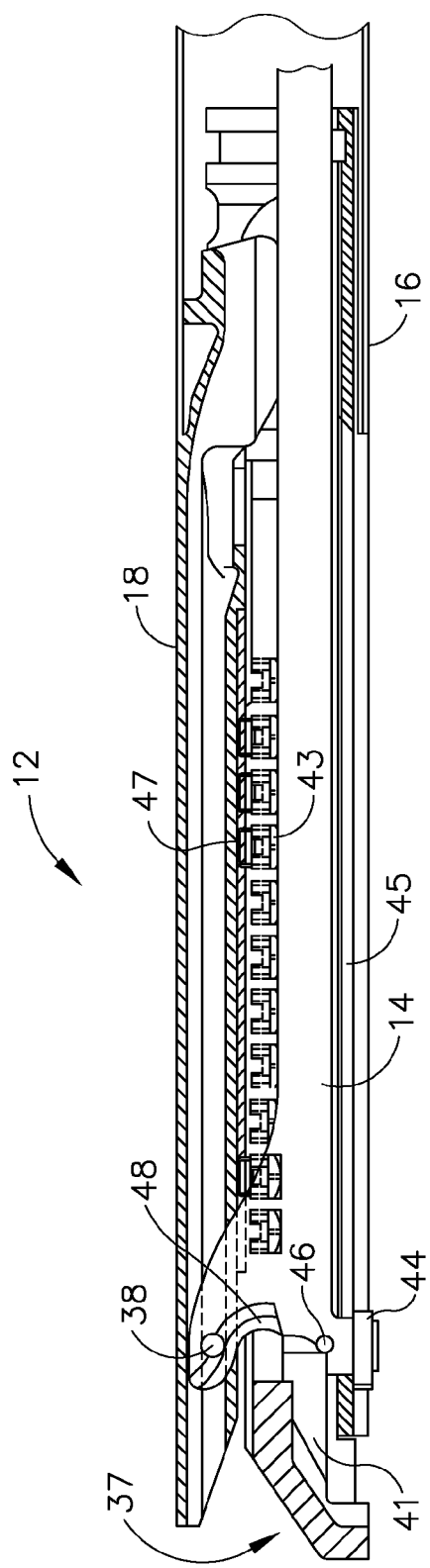
FIG. 4B depicts a side cross-sectional view of the end effector of FIG. 3, taken along line 4-4 of FIG. 3, with the firing beam in a distal position.
Figure 5:
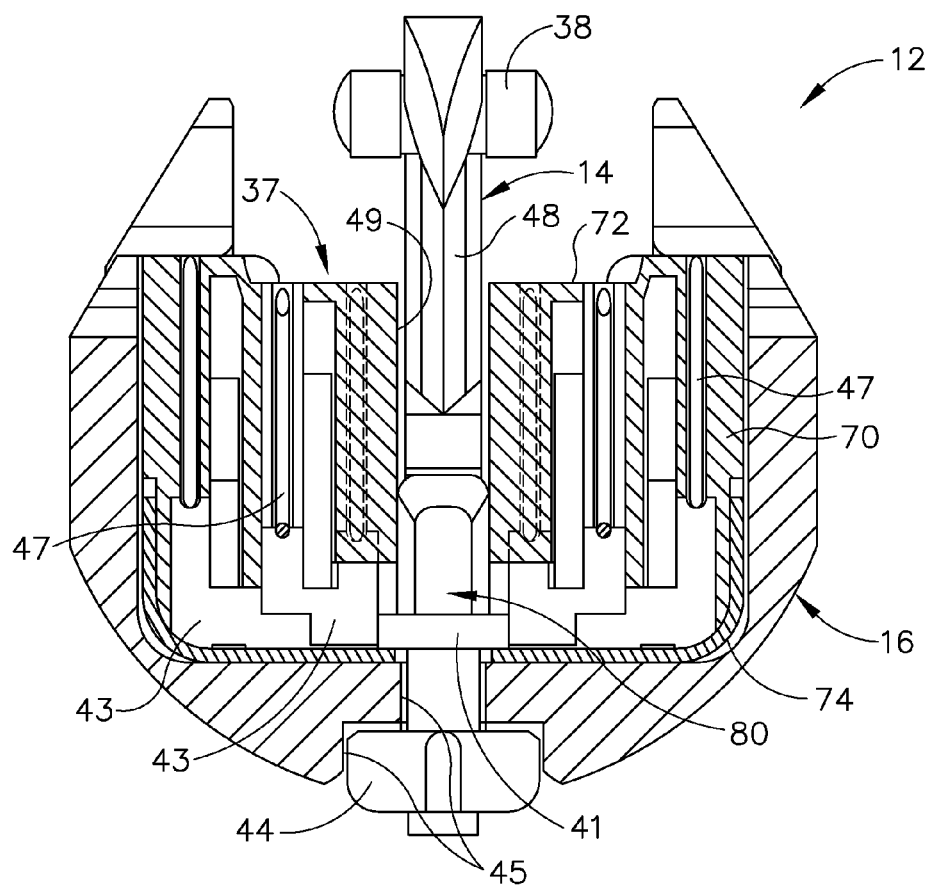
FIG. 5 depicts an end cross-sectional view of the end effector of FIG. 3, taken along line 5-5 of FIG. 3.
Figure 6:
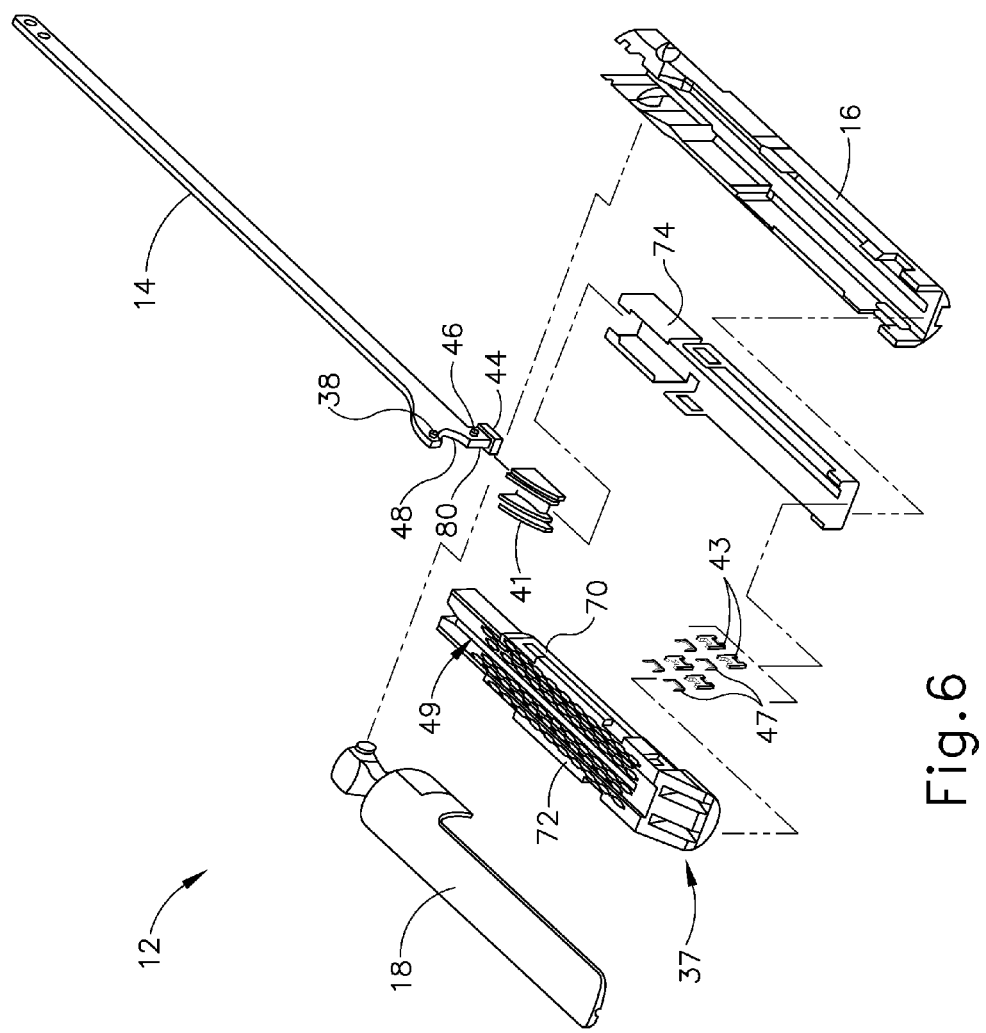
FIG. 6 depicts an exploded perspective view of the end effector of FIG. 3.

FIG. 3 shows firing beam (14) of the present example proximally positioned and anvil (18) pivoted to an open position, allowing an unspent staple cartridge (37) to be removably installed into a channel of lower jaw (16). As best seen in FIGS. 5-6, staple cartridge (37) of this example includes a cartridge body (70), which presents an upper deck (72) and is coupled with a lower cartridge tray (74). As best seen in FIG. 3, a vertical slot (49) is formed through part of staple cartridge (37). As also best seen in FIG. 3, three rows of staple apertures (51) are formed through upper deck (72) on one side of vertical slot (49), with another set of three rows of staple apertures (51) being formed through upper deck (72) on the other side of vertical slot (49). Of course, any other suitable number of staple rows (e.g., two rows, four rows, any other number) may be provided. Referring back to FIGS. 4A-6, a wedge sled (41) and a plurality of staple drivers (43) are captured between cartridge body (70) and tray (74), with wedge sled (41) being located proximal to staple drivers (43). Wedge sled (41) is movable longitudinally within staple cartridge (37); while staple drivers (43) are movable vertically within staple cartridge (37). Staples (47) are also positioned within cartridge body (70), above corresponding staple drivers (43). In particular, each staple (47) is driven vertically within cartridge body (70) by a staple driver (43) to drive staple (47) out through an associated staple aperture (51). As best seen in FIGS. 4A-4B and 6, wedge sled (41) presents inclined cam surfaces that urge staple drivers (43) upwardly as wedge sled (41) is driven distally through staple cartridge (37).

In some versions, staple cartridge (37) is constructed and operable in accordance with at least some of the teachings of U.S. patent application Ser. No. 13/780,106, entitled "Integrated Tissue Positioning and Jaw Alignment Features for Surgical Stapler," filed on even date herewith, published as U.S. Pat. Pub. No. 2014/0239042 on Aug. 28, 2014, the disclosure of which is incorporated by reference herein. In addition or in the alternative, staple cartridge (37) may be constructed and operable in accordance with at least some of the teachings of U.S. patent application Ser. No. 13/780,417, entitled "Installation Features for Surgical Instrument End Effector Cartridge," filed on even date herewith, published as U.S. Pat. Pub. No. 2014/0239044 on Aug. 28, 2014, the disclosure of which is incorporated by reference herein. Other suitable forms that staple cartridge (37) may take will be apparent to those of ordinary skill in the art in view of the teachings herein.

With end effector (12) closed as depicted in FIGS. 4A-4B by distally advancing closure tube (32) and closure ring (33), firing beam (14) is then advanced in engagement with anvil (18) by having upper pin (38) enter longitudinal anvil slot (42). A pusher block (80) (shown in FIG. 5) is located at the distal end of firing beam (14), and is configured to engage wedge sled (41) such that wedge sled (41) is pushed distally by pusher block (80) as firing beam (14) is advanced distally through staple cartridge (37) when firing trigger (28) is actuated. During such firing, cutting edge (48) of firing beam (14) enters vertical slot (49) of staple cartridge (37), severing tissue clamped between staple cartridge (37) and anvil (18). As shown in FIGS. 4A-4B, middle pin (46) and pusher block (80) together actuate staple cartridge (37) by entering into vertical slot (49) within staple cartridge (37), driving wedge sled (41) into upward camming contact with staple drivers (43) that in turn drive staples (47) out through staple apertures (51) and into forming contact with staple forming pockets (53) (shown in FIG. 3) on the inner surface of anvil (18). FIG. 4B depicts firing beam (14) fully distally translated after completing severing and stapling of tissue. It should be understood that staple forming pockets (53) are intentionally omitted from the view in FIGS. 4A-4B; but staple forming pockets (53) are shown in FIG. 3. It should also be understood that anvil (18) is intentionally omitted from the view in FIG. 5.

Figure 7:
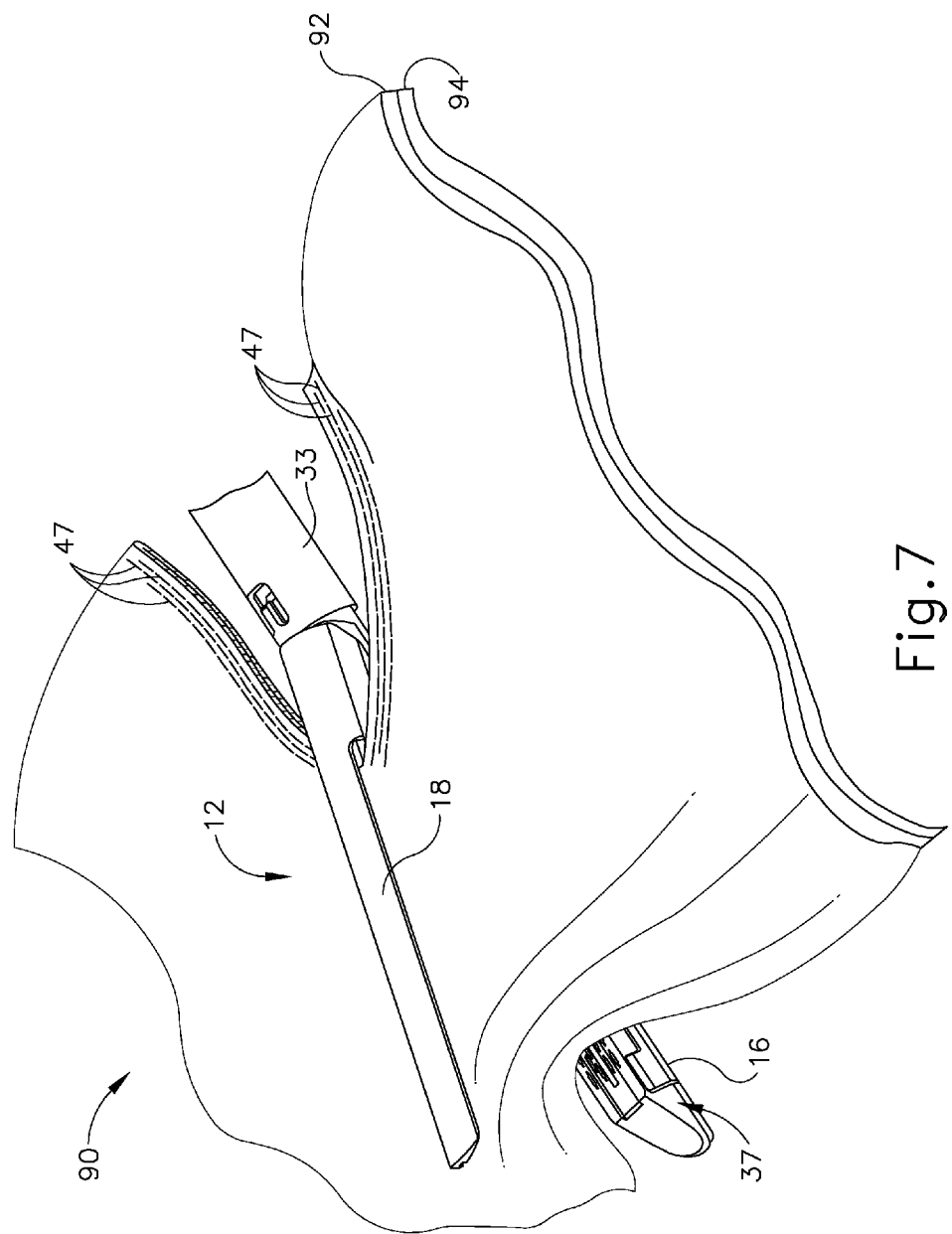
FIG. 7 depicts a perspective view of the end effector of FIG. 3, positioned at tissue and having been actuated once in the tissue.

FIG. 7 shows end effector (12) having been actuated through a single stroke through tissue (90). As shown, cutting edge (48) (obscured in FIG. 7) has cut through tissue (90), while staple drivers (43) have driven three alternating rows of staples (47) through the tissue (90) on each side of the cut line produced by cutting edge (48). Staples (47) are all oriented substantially parallel to the cut line in this example, though it should be understood that staples (47) may be positioned at any suitable orientations. In the present example, end effector (12) is withdrawn from the trocar after the first stroke is complete, spent staple cartridge (37) is replaced with a new staple cartridge, and end effector (12) is then again inserted through the trocar to reach the stapling site for further cutting and stapling. This process may be repeated until the desired amount of cuts and staples (47) have been provided. Anvil (18) may need to be closed to facilitate insertion and withdrawal through the trocar; and anvil (18) may need to be opened to facilitate replacement of staple cartridge (37).

It should be understood that cutting edge (48) may sever tissue substantially contemporaneously with staples (47) being driven through tissue during each actuation stroke. In the present example, cutting edge (48) just slightly lags behind driving of staples (47), such that a staple (47) is driven through the tissue just before cutting edge (48) passes through the same region of tissue, though it should be understood that this order may be reversed or that cutting edge (48) may be directly synchronized with adjacent staples. While FIG. 7 shows end effector (12) being actuated in two layers (92, 94) of tissue (90), it should be understood that end effector (12) may be actuated through a single layer of tissue (90) or more than two layers (92, 94) of tissue. It should also be understood that the formation and positioning of staples (47) adjacent to the cut line produced by cutting edge (48) may substantially seal the tissue at the cut line, thereby reducing or preventing bleeding and/or leaking of other bodily fluids at the cut line. Furthermore, while FIG. 7 shows end effector (12) being actuated in two substantially flat, apposed planar layers (92, 94) of tissue, it should be understood that end effector (12) may also be actuated across a tubular structure such as a blood vessel, a section of the gastrointestinal tract, etc. FIG. 7 should therefore not be viewed as demonstrating any limitation on the contemplated uses for end effector (12). Various suitable settings and procedures in which instrument (10) may be used will be apparent to those of ordinary skill in the art in view of the teachings herein.

It should be understood that instrument (10) may be configured and operable in accordance with any of the teachings of U.S. Pat. No. 4,805,823; U.S. Pat. No. 5,415,334; U.S. Pat. No. 5,465,895; U.S. Pat. No. 5,597,107; U.S. Pat. No. 5,632,432; U.S. Pat. No. 5,673,840; U.S. Pat. No. 5,704,534; U.S. Pat. No. 5,814,055; U.S. Pat. No. 6,978,921; U.S. Pat. No. 7,000,818; U.S. Pat. No. 7,143,923; U.S. Pat. No. 7,303,108; U.S. Pat. No. 7,367,485; U.S. Pat. No. 7,380,695; U.S. Pat. No. 7,380,696; U.S. Pat. No. 7,404,508; U.S. Pat. No. 7,434,715; U.S. Pat. No. 7,721,930; U.S. Pub. No. 2010/0264193 (now U.S. Pat. No. 8,408,439); and/or 2012/0239012 (now U.S. Pat. No. 8,453,914). As noted above, the disclosures of each of those patents and publications are incorporated by reference herein. Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the patents/publications cited herein will be apparent to those of ordinary skill in the art. It should also be understood that the below teachings are not limited to instrument (10) or devices taught in the patents cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. Exemplary Motorized Drive Features

Figure 8:
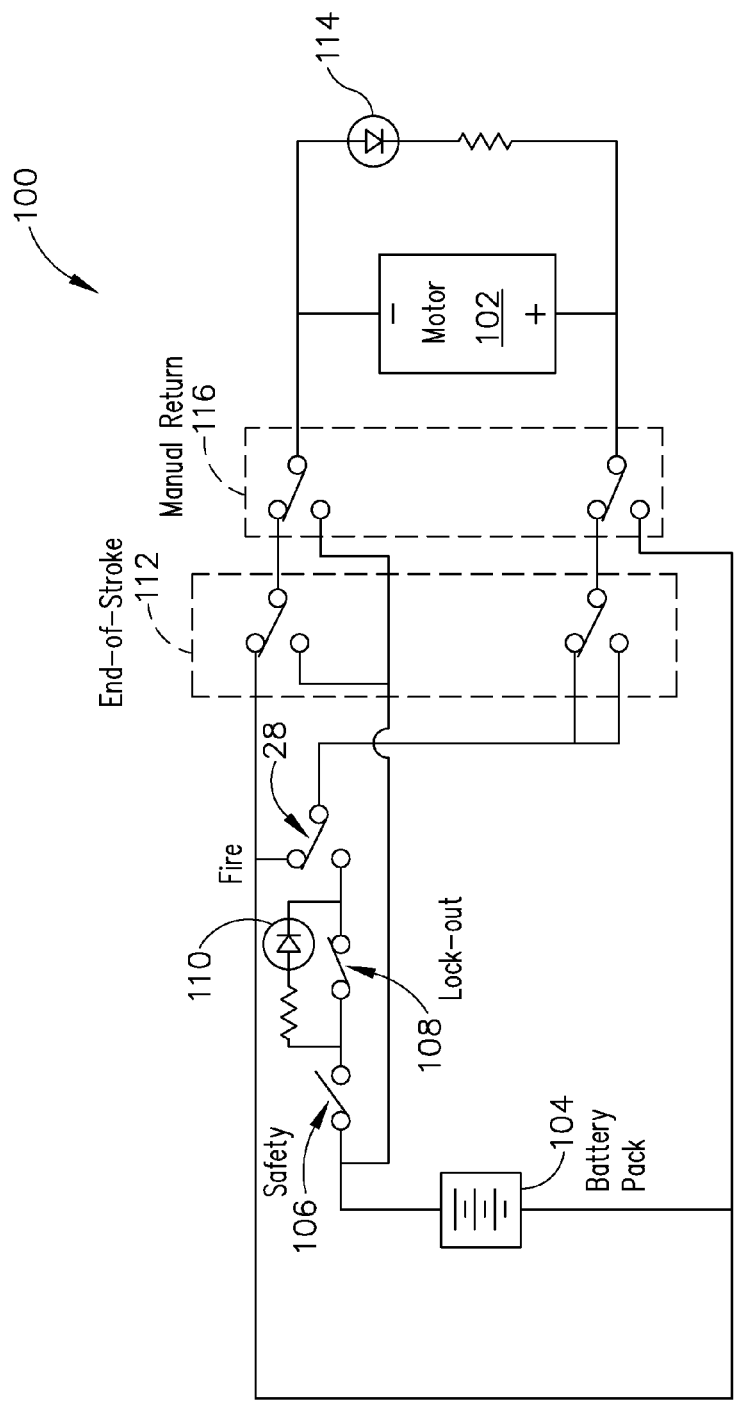
FIG. 8 depicts a schematic view of an exemplary control circuit for use in the instrument of FIG. 1.

In the present example, instrument (10) provides motorized control of firing beam (14). FIGS. 8-11 show exemplary components that may be used to provide motorized control of firing beam (14). In particular, FIG. 8 shows an exemplary control circuit (100) that may be used to power an electric motor (102) with electric power from a battery pack (104) (also shown in FIGS. 1-2). Electric motor (102) is operable to translate firing beam (14) longitudinally as will be described in greater detail below. It should be understood that the entire control circuit (100), including motor (102) and battery pack (104), may be housed within handle portion (20). FIG. 8 shows firing trigger (28) as an open switch, though it should be understood that this switch is closed when firing trigger (28) is actuated. Circuit (100) of this example also includes a safety switch (106) that must be closed in order to complete circuit (100), though it should be understood that safety switch (106) is merely optional. Safety switch (106) may be closed by actuating a separate button, slider, or other feature on handle portion (20).

Circuit (100) of the present example also includes a lockout switch (108), which is configured to be closed by default but is automatically opened in response to a lockout condition. By way of example only, a lockout condition may include one or more of the following: the absence of a cartridge (37) in lower jaw (16), the presence of a spent (e.g., previously fired) cartridge (37) in lower jaw (16), an insufficiently closed anvil (18), a determination that instrument (10) has been fired too many times, and/or any other suitable conditions. Various sensors, algorithms, and other features that may be used to detect lockout conditions will be apparent to those of ordinary skill in the art in view of the teachings herein. Similarly, other suitable kinds of lockout conditions will be apparent to those of ordinary skill in the art in view of the teachings herein. It should be understood that circuit (100) is opened and thus motor (102) is inoperable when lockout switch (108) is opened. A lockout indicator (110) (e.g., an LED, etc.) is operable to provide a visual indication of the status of lockout switch (108). By way of example only, lockout switch (108), lockout indicator (110), and associated components/functionality may be configured in accordance with at least some of the teachings of U.S. Pat. No. 7,644,848, entitled "Electronic Lockouts and Surgical Instrument Including Same," issued Jan. 12, 2010, the disclosure of which is incorporated by reference herein.

Once firing beam (14) reaches a distal-most position (e.g., at the end of a cutting stroke), an end-of-stroke switch (112) is automatically switched to a closed position, reversing the polarity of the voltage applied to motor (102). This reverses the direction of rotation of motor (102), it being understood that the operator will have released firing trigger (28) at this stage of operation. In this operational state, current flows through a reverse direction indicator (114) (e.g., an LED, etc.) to provide a visual indication to the operator that motor (102) rotation has been reversed. Various suitable ways in which end-of-stroke switch (112) may be automatically switched to a closed position when firing beam (14) reaches a distal-most position will be apparent to those of ordinary skill in the art in view of the teachings herein. Similarly, various suitable forms that reverse direction indicator (114) may take will be apparent to those of ordinary skill in the art in view of the teachings herein.

Handle portion (20) of the present example also includes a manual return switch (116), which is also shown in circuit (100). Manual return switch (116) is configured to act as a "bailout" feature, enabling the operator to quickly begin retracting firing beam (14) proximally during a firing stroke. In other words, manual return switch (116) may be manually actuated when firing beam (14) has only been partially advanced distally. Manual return switch (116) may provide functionality similar to end-of-stroke switch (112), reversing the polarity of the voltage applied to motor (102) to thereby reverse the direction of rotation of motor (102). Again, this reversal may be visually indicated through reverse direction indicator (114).

In some versions, one or more of switches (28, 106, 108, 112, 116) are in the form of microswitches. Other suitable forms will be apparent to those of ordinary skill in the art in view of the teachings herein. In addition to or in lieu of the foregoing, at least part of circuit (100) may be configured in accordance with at least some of the teachings of U.S. Pat. No. 8,210,411, entitled "Motor-Driven Surgical Instrument," issued Jul. 3, 2012, the disclosure of which is incorporated by reference herein.

Figure 9:
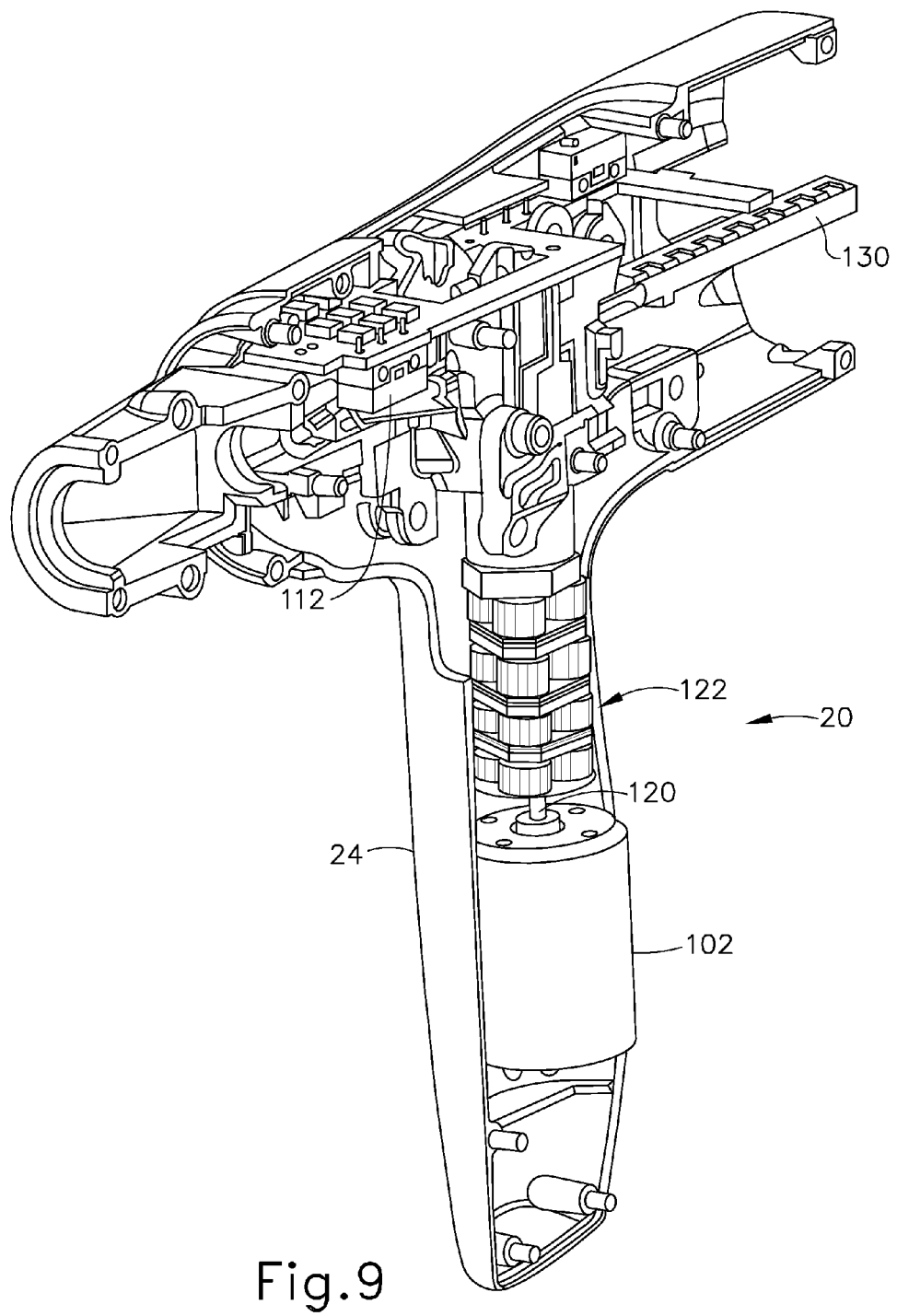
FIG. 9 depicts a perspective view of the handle assembly of the instrument of FIG. 1, with a housing half removed.
Figure 10:
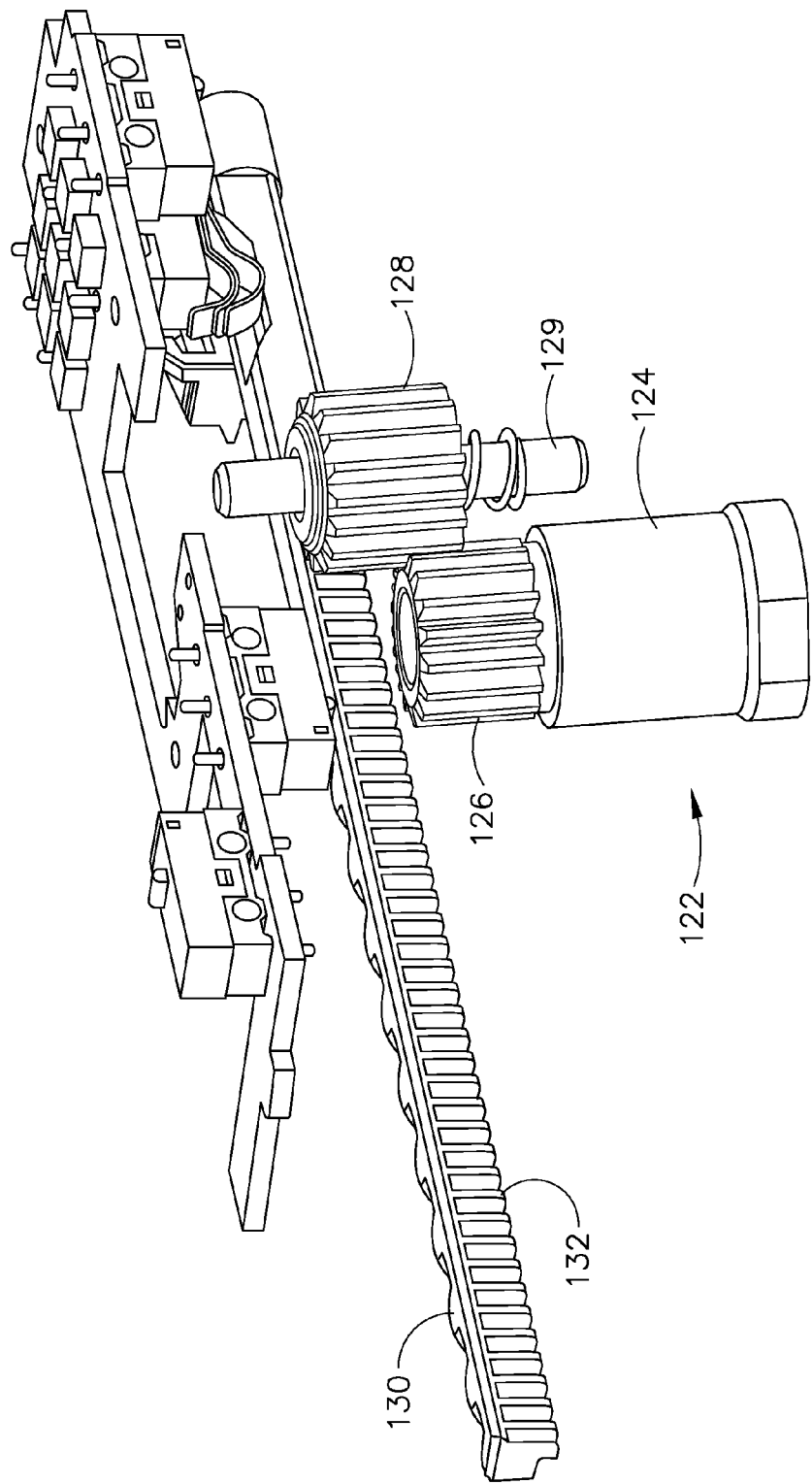
FIG. 10 depicts a perspective view of drive assembly components from the handle assembly of FIG. 9.
Figure 11:
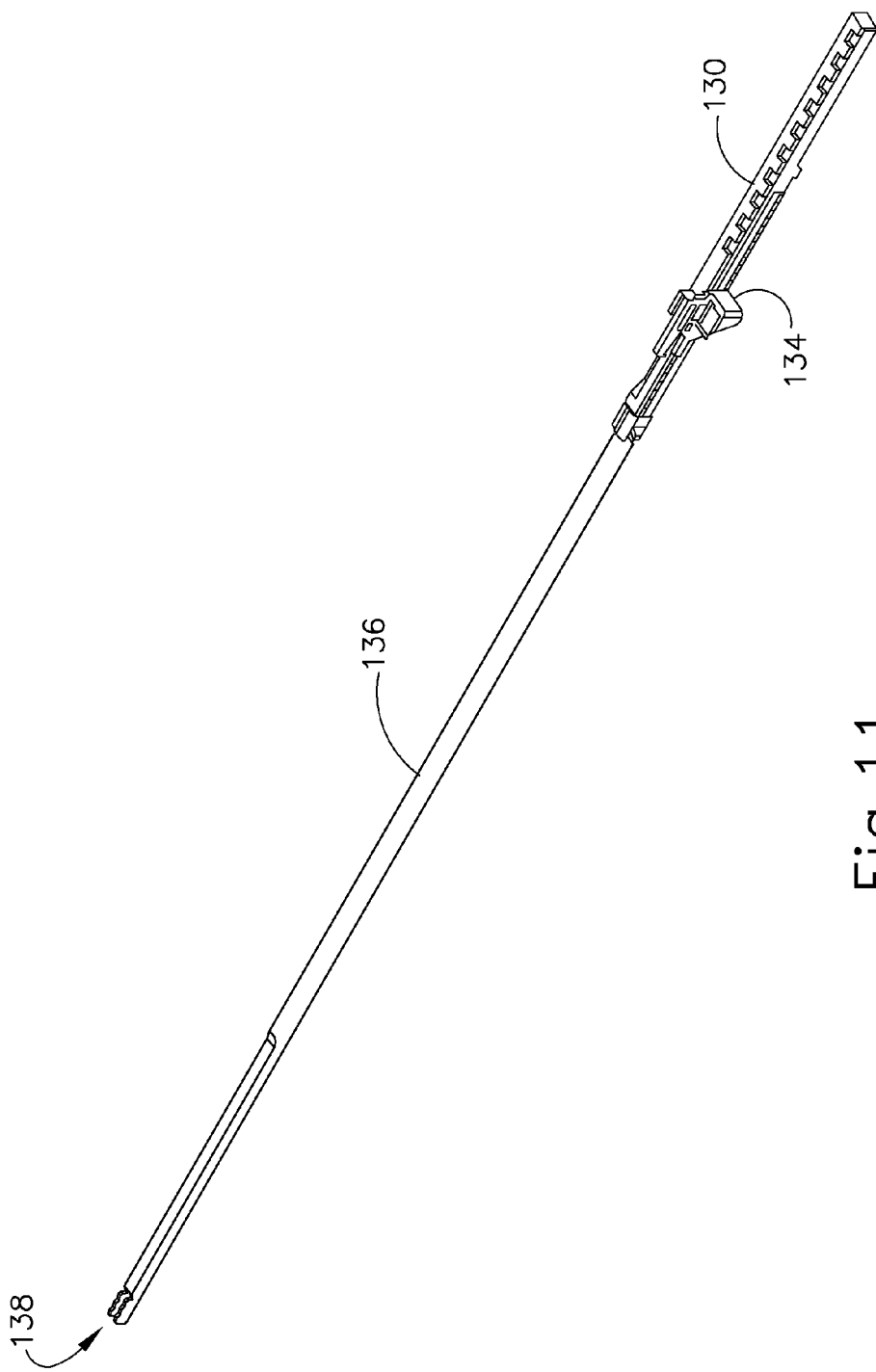
FIG. 11 depicts a perspective view of an elongate member from the drive assembly of FIG. 10.

FIGS. 9-11 show various mechanical components that may be used to provide motorized translation of firing beam (14). In particular, FIG. 9 shows motor (102) housed in pistol grip (24) of handle portion (20). It should be understood that battery pack (104) (shown in FIGS. 1-2) may also be located in pistol grip (24) (e.g., below motor (102)) and/or elsewhere within handle portion (20). Motor (102) has a drive shaft (120) that is coupled with a gear assembly (122). Gear assembly (122) has an external casing (not shown) and is operable to drive an upper gear (126), which is shown in FIG. 10. Upper gear (126) meshes with a pinion (128), which is rotatably supported by a pin (129) secured in handle portion (20). It should therefore be understood that activation of motor (102) will ultimately rotate pinion (128) within handle portion (20).

As also shown in FIGS. 9-10, a translating rack (130) includes teeth (132) that mesh with pinion (128), such that rack (130) translates longitudinally when pinion (128) rotates. As shown in FIG. 11, rack (130) is coupled with an elongate member (136), which extends through shaft (22) and includes a distal end (138) that couples with the proximal end of firing beam (14). Elongate member (136) translates within shaft (22), such that elongate member (136) communicates longitudinal motion of rack (130) to firing beam (14). It should therefore be understood that activation of motor (102) will ultimately translate firing beam (14) within end effector (12). In particular, motor (102) may drive firing beam (14) distally to sever tissue (90) and drive staples (47) into tissue (90). A switch actuation arm (134) extends laterally from rack (130), and is positioned to engage end-of-stroke switch (112) when firing beam (14) reaches a distal-most position (e.g., after tissue (90) has been severed and staples (47) have been driven into tissue (90)). As noted above, this engagement of end-of-stroke switch (112) automatically reverses motor (102) to return firing beam (14) from the distal-most position to the proximal position, enabling anvil (18) to be pivoted away from lower jaw (16) to release tissue (90).

Use of the term "pivot" (and similar terms with "pivot" as a base) should not be read as necessarily requiring pivotal movement about a fixed axis. In some versions, anvil (18) pivots about an axis that is defined by a pin (or similar feature) that slides along an elongate slot or channel as anvil (18) moves toward lower jaw (16). In such versions, the pivot axis translates along the path defined by the slot or channel while anvil (18) simultaneously pivots about that axis. In addition or in the alternative, the pivot axis may slide along the slot/channel first, with anvil (18) then pivoting about the pivot axis after the pivot axis has slid a certain distance along the slot/channel. It should be understood that such sliding/translating pivotal movement is encompassed within terms such as "pivot," "pivots," "pivotal," "pivotable," "pivoting," and the like. Of course, some versions may provide pivotal movement of anvil (18) about an axis that remains fixed and does not translate within a slot or channel, etc.

In addition to or in lieu of the foregoing, the features operable to drive firing beam (14) may be configured in accordance with at least some of the teachings of U.S. Pub. No. 2012/0239012 (now U.S. Pat. No. 8,453,914), the disclosure of which is incorporated by reference herein; and/or in accordance with at least some of the teachings of U.S. Pub. No. 2012/0239012 (now U.S. Pat. No. 8,453,914), the disclosure of which is also incorporated by reference herein. Other suitable components, features, and configurations for providing motorization of firing beam (14) will be apparent to those of ordinary skill in the art in view of the teachings herein. It should also be understood that some other versions may provide manual driving of firing beam (14), such that a motor may be omitted. By way of example only, firing beam (14) may be actuated in accordance with at least some of the teachings of any other patent/publication reference cited herein.

III. Exemplary End Effector with Visualization and Lead-In Features

It will be understood that in some instances, it may be desirable to provide the user with better visualization of end effector (12). In particular, as end effector (12) is inserted into a surgical site, the user may rotate shaft (22) of instrument (10) during the procedure. As a result, end effector (12) also rotates. As end effector (12) rotates, it may be desirable for the user to have visual access to the surgical site. For instance, the user may wish to see the interface or contact between tissue (90) and end effector (12). Since end effector (12) may be rotated about the longitudinal axis (LA) relative to handle portion (20), it will be understood that the user may view the surgical site such that lower jaw (16) of end effector is visible rather than anvil (18). Alternatively, end effector (12) could be rotated such that when the user views end effector (12), anvil (18) is visible by the user. It may be desirable to provide visibility of the surgical site for the user beyond what is possible in instrument (10) of FIG. 1. For instance, in the case of some surgical procedures where fluid carrying vessels are transected and stapled, it may be desirable to have visual confirmation that anvil (18) and lower jaw (16) completely cover the vessel to be cut, such that the vessel may be fully cut and stapled in one single actuation. In other words, the user may wish to avoid cutting and stapling only a portion of a vessel. Thus, some means of visual monitoring and/or feedback may be desirable so that the user will know that end effector (12) has been positioned properly within the surgical site for anvil (18) and lower jaw (16) to fully clamp the vessel. One potential way of monitoring the surgical site may include improving visualization of the area adjacent to the distal tip of lower jaw (16) and anvil (18). Furthermore, it will be understood that not only visualization of the distal end of end effector (12) may be desirable. It may also be desirable to construct end effector (12) such that as end effector (12) is urged through tissue, end effector (12) has features operable to promote smooth and atraumatic movement of end effector (12) through tissue.

Figure 12:
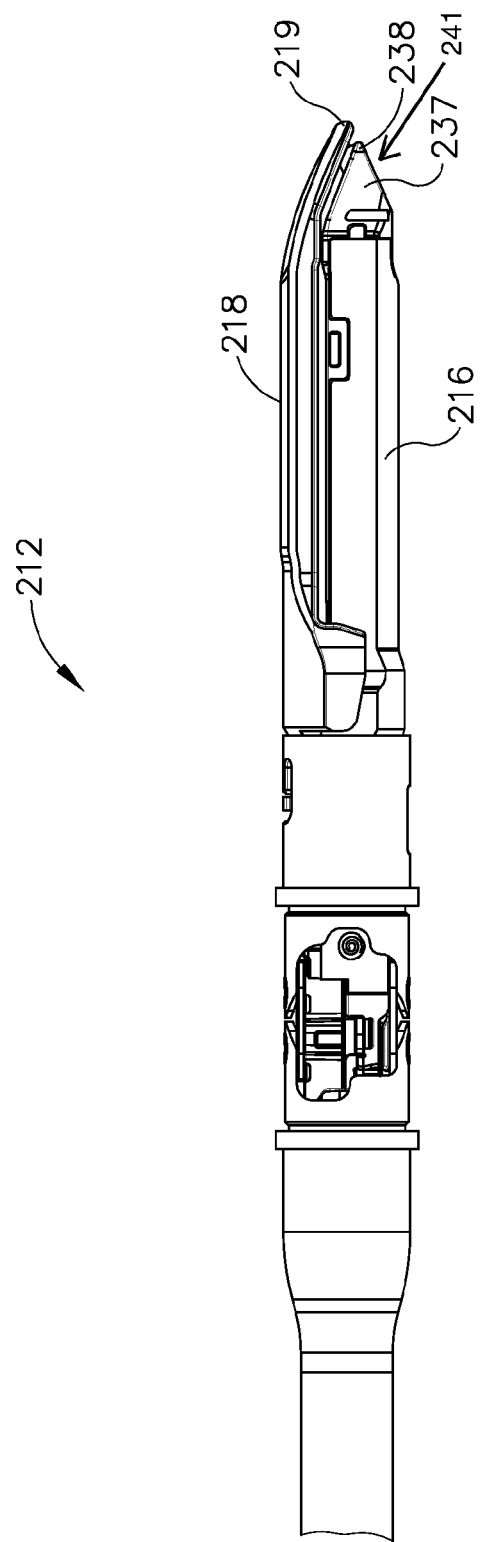
FIG. 12 depicts a side, elevational view of an alternative version of an end effector with an angled anvil and an angled cartridge.

FIG. 12 depicts an exemplary end effector (212) comprising an anvil (218) and a lower jaw (216). It will be appreciated that end effector (212) may be used interchangeably with end effector (12) of instrument (10). End effector (212) may be integrally formed with instrument (10) or in the alternative may be interchangeable with end effector (12) of instrument (10).

Anvil (218) is operable to pivot relative to lower jaw (216). Anvil (218) and lower jaw (216) may clamp tissue (90) similarly to clamping performed by anvil (18) and lower jaw (16) shown in FIG. 1. End effector (212) further comprises a cartridge (237) operable to be placed in lower jaw (216) similarly to cartridge (37) shown in FIG. 3.

Figure 13:
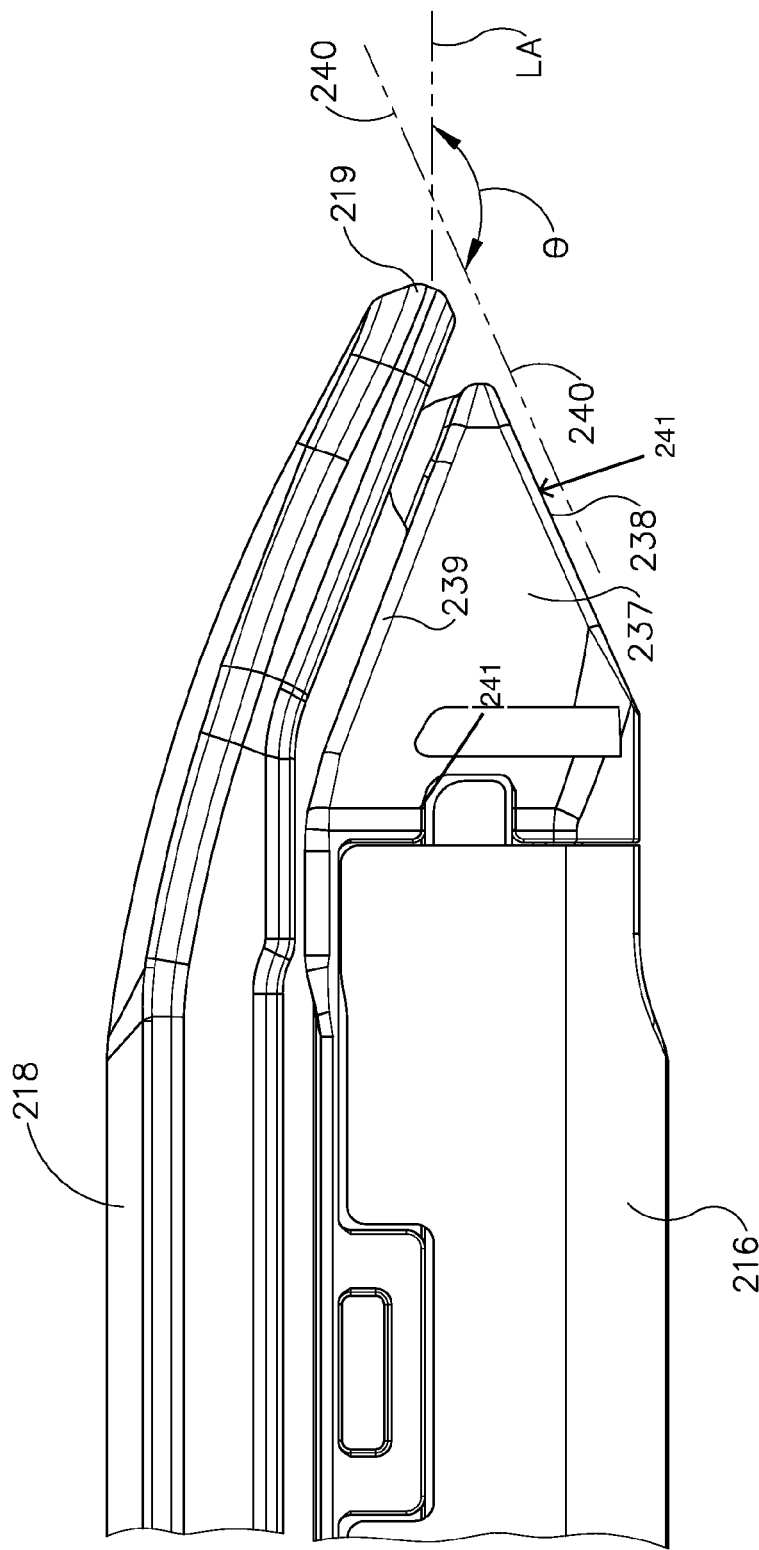
FIG. 13 depicts an enlarged, side view of the end effector of FIG. 12.

Anvil (218) as can be seen in FIGS. 12-13 has an elongated shape where the distal portion of anvil (218) angles toward cartridge (237). The distal portion of anvil (218) angles toward cartridge (237) such that the distal most tip (219) of anvil (218) extends distally longitudinally further than cartridge (237). Though it will be understood that in some versions, distal tip (219) may extend to a distance longitudinally equal to cartridge (237) or proximal relative to the distal most point on cartridge (237). Furthermore, anvil (218) angles toward cartridge (237) through a gentle slope. By way of example, anvil (218) is shaped in FIG. 12 similarly to an inverted ski tip. It will be understood that the angled shape of anvil (218) may provide easier insertion of end effector (212) into a surgical site. For instance, the gentle slope or inverted ski tip shape of anvil (218) may provide an atraumatic tissue deflection surface as anvil (218) contacts or moves through tissue. Once placed into a surgical site, it will be understood that the angled shape of anvil (218) may provide better maneuverability of end effector (212). Other suitable variations of anvil (218) will be apparent to one of ordinary skill in the art in view of the teachings herein.

Figure 14:
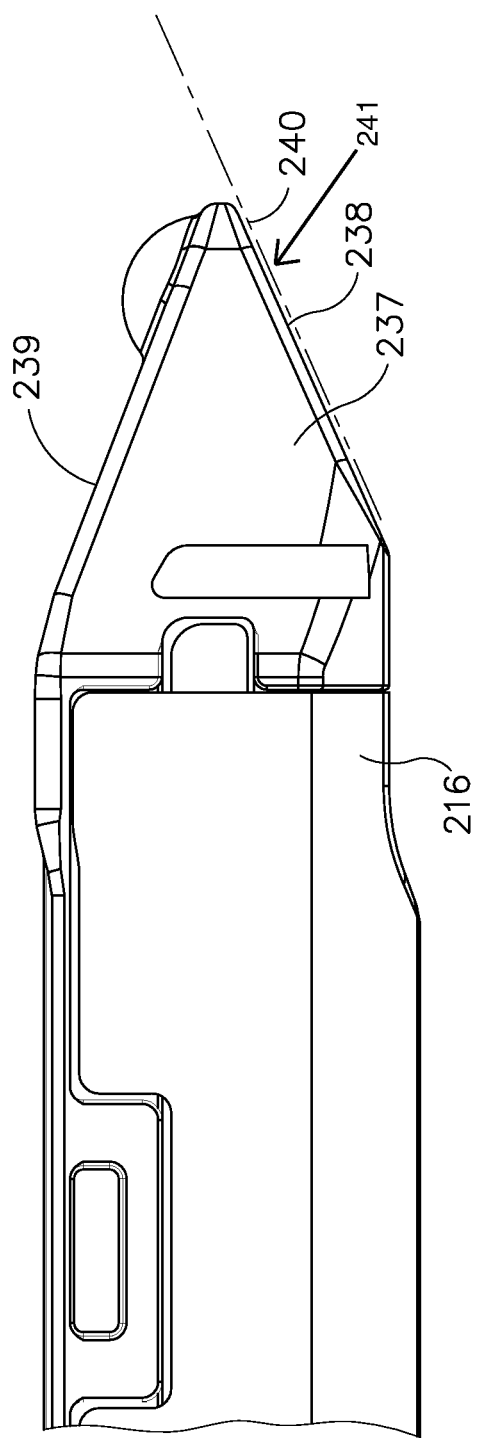
FIG. 14 depicts an enlarged side view of the cartridge of FIG. 12 showing an angled tip.

Cartridge (237) is operable to hold staples similar to staples (47) shown in FIG. 4A for driving into tissue. As shown in FIG. 13, the distal end (241) of cartridge (237) has a triangular profile. In particular, the distal end (241) of cartridge (237) comprises an upper tapered surface (239) and a lower tapered surface (238). Upper tapered surface (239) and lower tapered surface (238) lead to the distal most end of cartridge (237). Lower tapered surface (238) defines a sight line (240) such that once end effector (212) is inserted into a surgical site, the user can see along sight line (240). Sight line (240), which can be seen more clearly in FIG. 14, extends along the edge of lower tapered surface (238). It will be appreciated that the planar shape of lower tapered surface (238) may be operable to allow the user to visualize and/or nearly visualize the distal tip (219) of anvil (218), In particular, sight line (240) intersects longitudinal axis (LA), which extends longitudinally through end effector (212), to form a viewing angle (θ).

It will be understood that viewing angle (θ) may establish the relative visibility that a user has regarding distal tip (219). In particular, the user can see in front of distal tip (219) along any line of sight that passes through the intersection of sight line (240) and longitudinal axis (LA) within viewing angle (θ). For instance, as viewing angle (θ) increases, the user would have greater visibility of the area immediately in front of distal tip (219) from proximal vantage points; whereas as viewing angle (θ) decreases, the user has less visibility of the area in front of distal tip (219) from proximal vantage points. In some versions, viewing angle (θ) defines an angle greater than 90 degrees. Additionally, in some versions, viewing angle (θ) defines an angle greater than 135 degrees. Other suitable angles for viewing angle (θ) will be apparent to one of ordinary skill in the art in view of the teachings herein. In the illustrated version, it will be understood that the user generally looks along sight line (240) or along some other line of sight within viewing angle (θ), thus, the user has visibility along sight line as well as any area within viewing angle (θ). The underside of distal tip (219) is further slightly rounded to aid in the visibility of the intersection of longitudinal axis (LA) and sight line (240).

When tissue (90) is clamped between a closed cartridge (237) and anvil (218) as seen in FIG. 13, the user can look along sight line (240) or elsewhere within viewing angle (θ) to see, for instance, precisely where anvil (218) has clamped tissue (90). Furthermore, the user would be able to determine whether the tissue is completely clamped between anvil (218) and cartridge (237) such that tissue does not spill over the end of end effector (212). It will be understood that the user may be able to also visualize the quality of the clamp between anvil (218) and cartridge (237) against tissue (90). It will be appreciated that in some instances, end effector (212) may be rotated before, during, or after clamping tissue (90). As a result, the tapered shape of anvil (218) may also provide more accessible viewing of distal tip (219) or substantially adjacent distal tip (219). It will be understood that the taper of anvil (218) along with lower tapered surface (238) of cartridge (237) may further promote easy insertion of end effector (212) into tissue in an atraumatic manner. Furthermore, it may be easier to fit end effector (212) through a trocar or other devices operable to introduce end effector (212) into a surgical site due to the tapered end of end effector (212). For instance, once distal tip (219) is fit into a trocar, lower tapered surface (238) and the tapered shape of anvil (218) may provide a lead-in, guiding the rest of end effector (212) into the trocar.

Figure 15A:
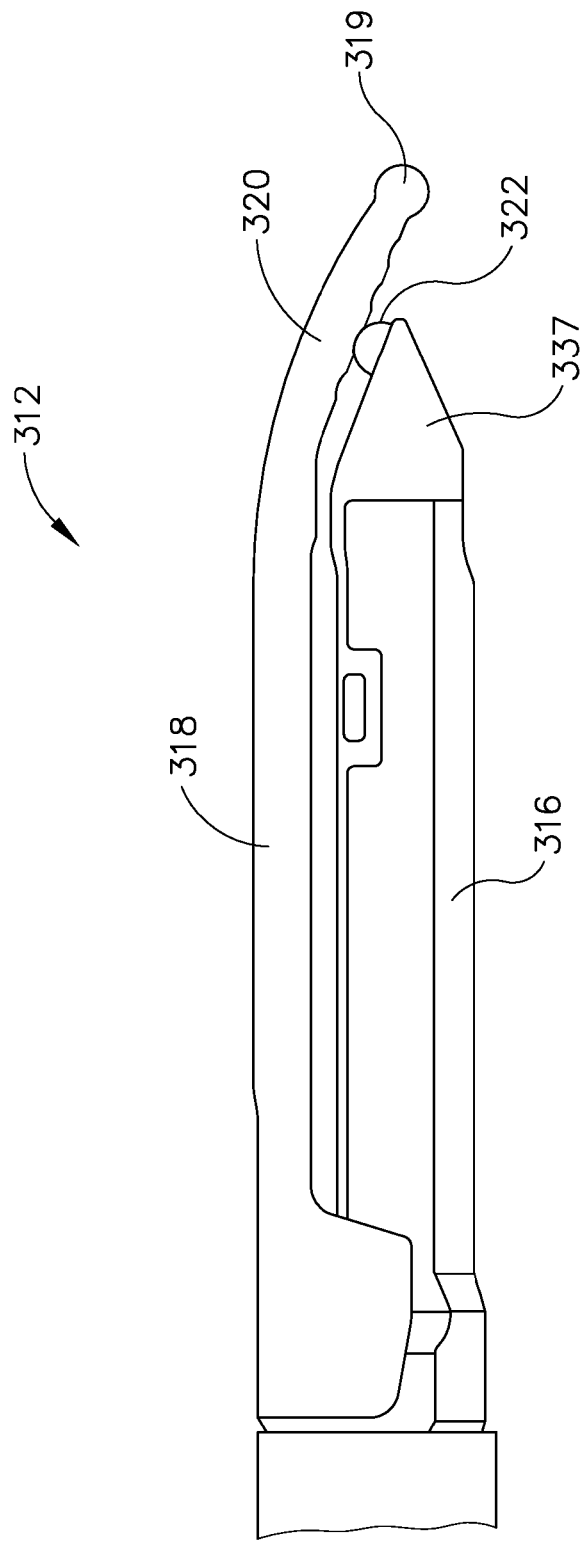
FIG. 15A depicts a side, elevation view of an exemplary alternative version of an end effector with an anvil with a ball tip and a cartridge with a ball tip, with the anvil in the closed position.
Figure 15B:
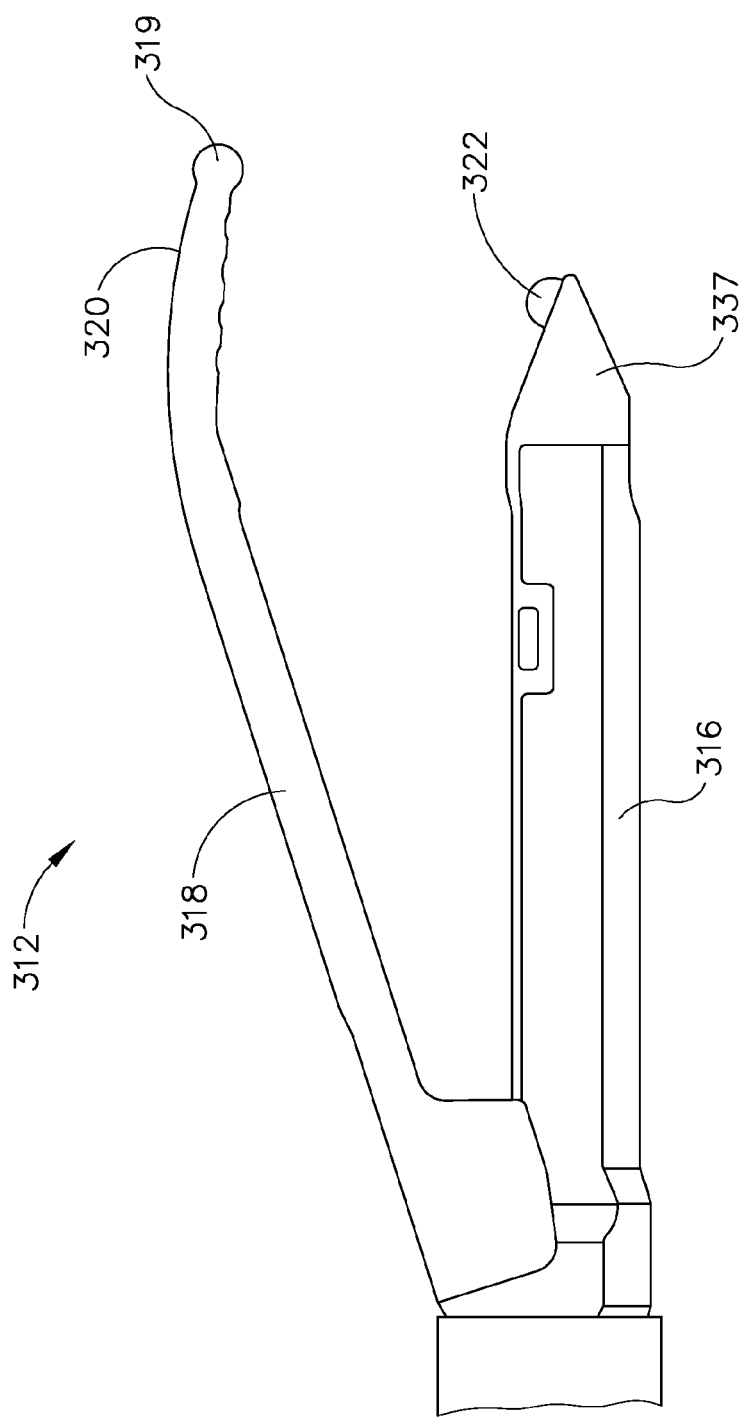
FIG. 15B depicts a side, elevation view of the end effector of FIG. 15A, with the anvil in an open position.

FIG. 15A shows an exemplary alternative version of an end effector (312) comprising an anvil (318) and a lower jaw (316). It will be appreciated that end effector (312) may be used in place of end effector (12) shown in FIG. 1. In some versions, end effector (312) may be integrally formed with shaft (22) or alternatively may be separately formed and then combined. Anvil (318) is operable to pivotally open and close in relation to cartridge (337). For instance, FIG. 15B shows anvil (318) in the open position and FIG. 15A shows anvil (318) in the closed position. Anvil (318) has an angled distal portion (320) and an anvil ball tip (319) at the distal most portion of angled distal portion (320). Cartridge (337) has a cartridge ball tip (322). It will be understood that cartridge ball tip (322) fits into the underside of anvil (318) as will be described in further detail below. It will be understood that, similar to end effector (212) shown in FIG. 12, the distal taper of anvil (318) and cartridge (337) provides improved visibility of the distal end of end effector (312).

Figure 16:
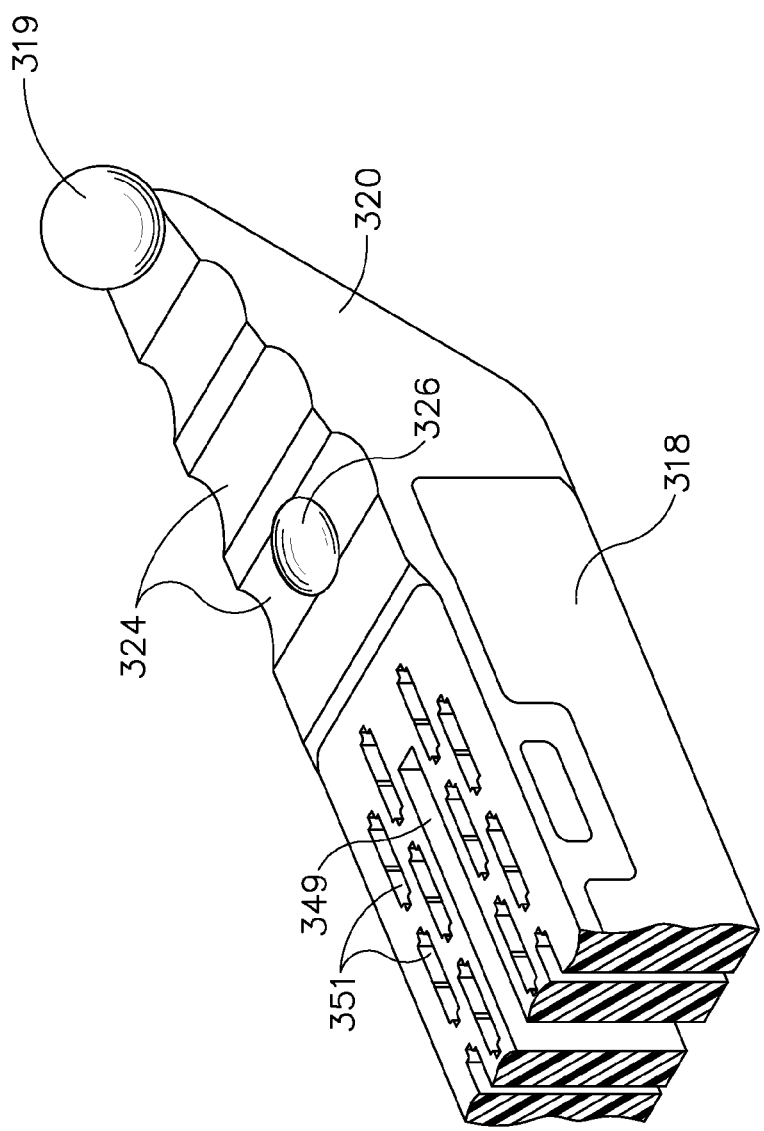
FIG. 16 depicts a side perspective view of the anvil of the end effector of FIG. 15A showing the inner portion with a ball groove and recesses.

FIG. 16 shows an enlarged view of the underside of anvil (318). In addition to anvil ball tip (319) and angled distal portion (320), anvil (318) comprises a plurality of transversely extending recesses (324) and a ball pocket (326).

Plurality of recesses (324) line angled distal portion (320). In the illustrated version, plurality of recesses (324) include three recesses, but it will be appreciated other suitable numbers of recesses (324) may be used. For instance, four, five, six, or more recesses (324) may be used. It will be appreciated that recesses (324) may be equally spaced apart. Furthermore, recesses (324) may be spaced apart by a known distance. For instance, the user may be aware that each of recesses (324) is spaced 1 mm apart from each other. As a result, when tissue is grasped between anvil (318) and cartridge (337), the tissue may cover a portion of recesses (324). Due to the tissue covering recesses (324), the user would be able to determine the approximate length of the tissue over recesses (324) by simply multiplying the number of covered recesses (324) by the distance between recesses (324). Alternatively, the user could assess the number of exposed recesses (324) to calculate the approximate distance from anvil ball tip (319) to tissue. Furthermore, it will be appreciated that recesses (324) are also operable to promote gripping of tissue such that anvil (318) and cartridge (337) are operable to maintain a more secure grip on tissue. Anvil (318) of the exemplary version also comprises staple apertures (351) and vertical slot (349). It will be understood that staple apertures (351) and vertical slot (349) function substantially similar to apertures (51) and vertical slot (349) of FIG. 3.

It will be appreciated that ball pocket (326) has a shape that complements cartridge ball tip (322). While pocket (326) and tip (322) have partially spherical shapes in the present example, it should be understood that any other suitable shapes may be used. In the present example, when anvil (318) closes onto cartridge (337), cartridge ball tip (322) engages ball pocket (326) and promotes alignment and stabilization of anvil (318) with cartridge (337) due to the complementary configurations of tip (322) and pocket (326). While ball pocket (326) is positioned in one of recesses (324) in the exemplary version, it will be understood that ball pocket (326) may be positioned in any suitable place along anvil (318). In some versions, ball pocket (326) or ball tip (322) may have a surface that is polished and/or painted such that when anvil (318) is inserted into tissue, the polished surface of ball pocket (326) or ball tip (322) provides the user with greater visibility of ball pocket (326) or ball tip (322). As a result, the user can better determine whether ball tip (322) or ball pocket (326) is sufficiently close to the targeted tissue area. Furthermore, while the exemplary version shows anvil (318) as having recesses (324) and ball pocket (326), it will be understood that cartridge (337) may in addition or in the alternative comprise a ball pocket similar to ball pocket (326) for receiving anvil ball tip (319) and may also have recesses substantially similar to recesses (324).

In addition to facilitating tip visibility of anvil (218) to the user, ball tip (322) may be used as a blunt dissection tool (e.g., as a button dissector) or as a tool for moving tissue around within a surgical site. It will be understood that the rounded shape of ball tip (322) is operable to provide an atraumatic surface to engage tissue. While the exemplary version shows a spherical shape for ball tip (322), it will be appreciated that any suitable atraumatic shape for ball tip (322) may be used as would be apparent to one of ordinary skill in the art in view of the teachings herein. By using ball tip (322), it will be understood that the user may be able to minimize tissue trauma as end effector (312) is pushed or otherwise moved through tissue.

Figure 17:
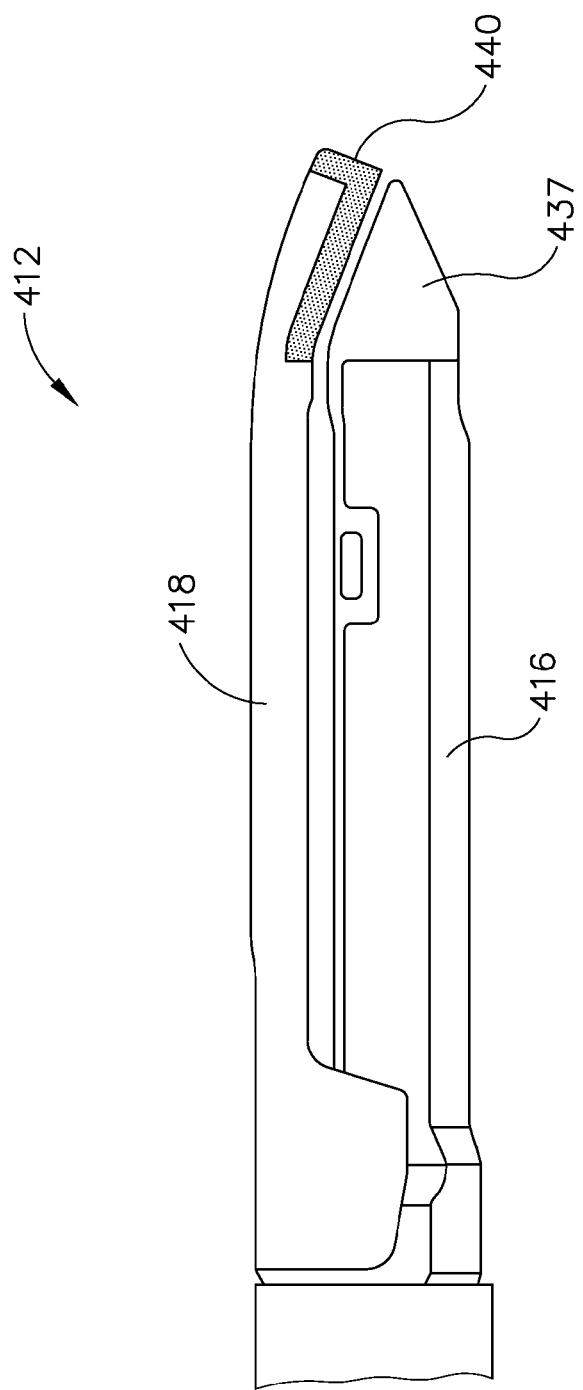
FIG. 17 depicts a side, elevation view of an exemplary alternative version of an end effector with a colored portion.
Figure 18:
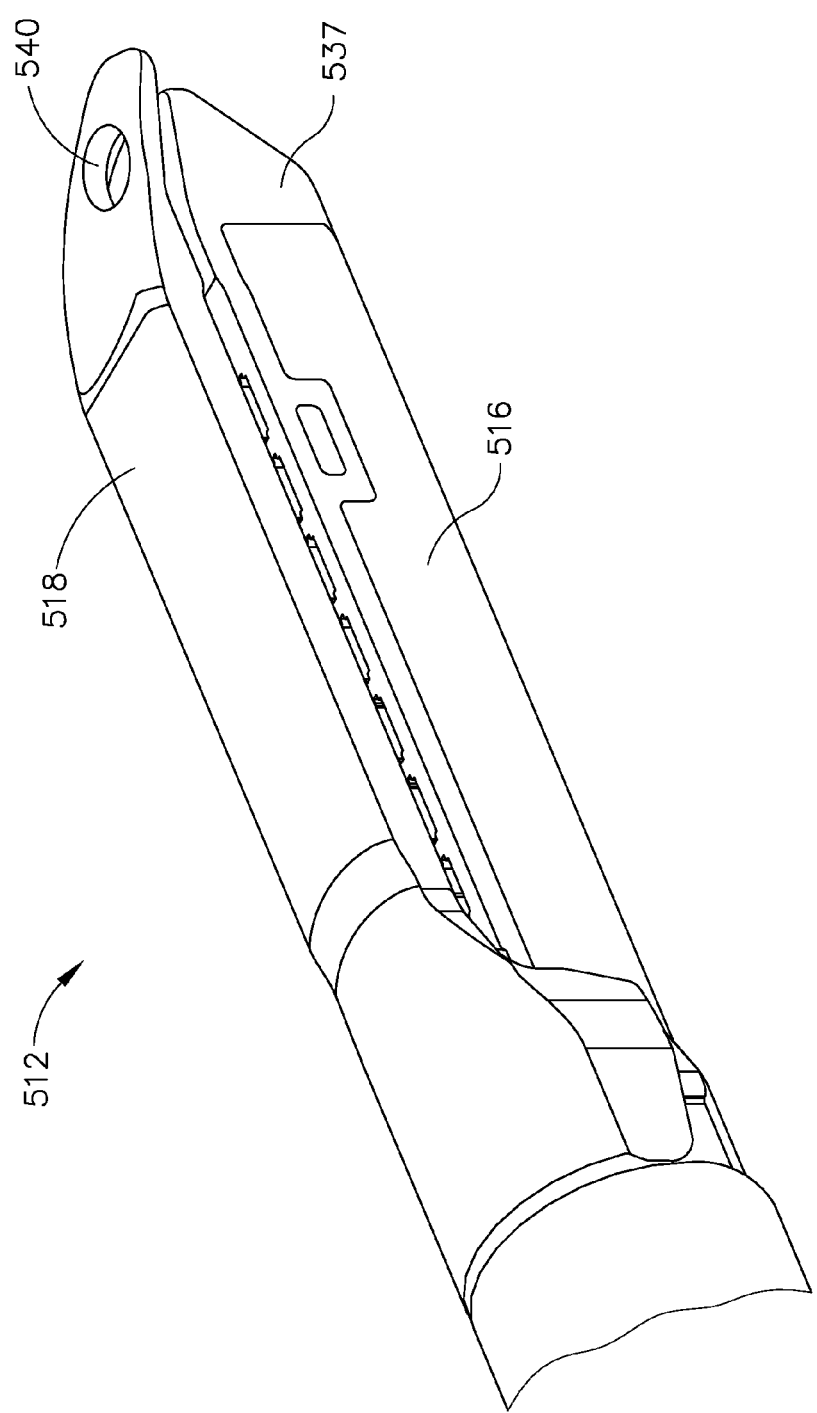
FIG. 18 depicts a side, perspective view of an exemplary alternative version of an end effector with an opening formed in the anvil.

In some instances it may be desirable to have an end effector with a more visible tip such that the user has improved visibility of the distal end of end effector as it is inserted, for instance, into a surgical site. FIGS. 17 and 18 depict end effectors (412, 512) designed to promote improved visibility at the distal end of end effectors (412). In FIG. 17, end effector (412) comprises an anvil (418) and lower jaw (416) where lower jaw (416) holds a cartridge (437). It will be appreciated that anvil (418), lower jaw (416), and cartridge (437) function in a substantially similar manner to anvil (18), lower jaw (16), and cartridge (37) of FIG. 3. Anvil (418) differs due to the angled shape of the distal end of anvil (418), and due to anvil (418) comprising a cap portion (440). Cap portion (440) comprises a rubber, plastic, or otherwise synthetic material operable to cover the end of anvil (418). For instance, cap portion (440) could include an insert, an overmold, a coating; or take any other suitable form as would be apparent to one of ordinary skill in the art in view of the teachings herein. In the exemplary version, cap portion (440) covers the underside of anvil (418). As a result, it will be appreciated that as tissue is squeezed by anvil (418), the amount of visible cap portion (440) may indicate to the user how much of tissue is being clamped by anvil (418). It will also be appreciated that cap portion (440) may comprise a contrasting color distinguishable from tissue. For instance, cap portion (440) may comprise a bright red, yellow, blue, green, etc. color such that once anvil (418) is inserted into tissue, the user can quickly determine the position of anvil (418) within the tissue. While in the exemplary version, anvil (418) comprises cap portion (440), it will be understood that in addition to or in the alternative, cartridge (437) may have a similar colored portion as well. Furthermore, while the illustrated version shows cap portion (440) as only covering a portion of anvil (418), in some version, the entire anvil (418) may be covered.

FIG. 18 depicts an alternative exemplary end effector (512) comprising an anvil (518) and lower jaw (516) where lower jaw (516) holds a cartridge (537). Anvil (518) defines an opening (540) at the distal end of anvil (518). It will be appreciated that opening (540) extends completely through anvil (518) such that as anvil (518) closes on tissue, the user can look to see whether tissue is visible through opening (540). In the event that tissue is visible, the user has at least one form of confirmation that tissue has been clamped between anvil (518) and cartridge (537). In some instances, it will be appreciated that the user may desire to see tissue through opening (540) only briefly, followed by no tissue. As a result, the user would have confirmation that tissue has been positioned deeply enough between anvil (518) and cartridge (537) to ensure that when the tissue is clamped and cut, clamping and cutting occurs across the entirety of the tissue between anvil (518) and cartridge (537) in a single firing of end effector (512). Such confirmation may be desirable, for instance, in the cutting of vessels. Furthermore, it will be appreciated that opening (540) also provides a disturbance in the surface of anvil (518) that may provide increased grip between anvil (518) and the tissue. While in the exemplary version anvil (518) forms opening (540), it will be appreciated that opening (540) may be formed on cartridge (537) or any other suitable portion of end effector (512) as would be suitable for providing visibility or gripping of tissue in between anvil (518) and cartridge (537). Furthermore, while opening (540) in the illustrated version is shown as a circular opening formed perpendicular to the surface of anvil (518), opening (540) may have any suitable shape and may be formed at any suitable angle through anvil (518) that promotes the visibility of tissue through opening (540).

In some versions, end effector (512) may be combined with end effector (412). In particular, opening (540) could provide an anchoring point for applying an overmold or securing an additional feature such as cap portion (440). Such an overmold or cap portion (440) may be formed of a material that is different from the material forming anvil (518). By way of example only, an overmold or cap portion (440) could be formed of plastic or other polymer while anvil (518) is formed of metal. It should also be understood that anvil (518) and/or any other feature of end effector (512) may include an applied coating or surface treatment. While the illustrated version is shown to include opening (540) on anvil (518), it will be understood that opening (540) could be positioned anywhere on the distal end of end effector (512) for receiving an overmold component such as cap portion (440). For instance, opening (540) could be positioned on the side of anvil (518) or on any suitable location on cartridge (537).

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pub. No. 2013/0012957, entitled "Automated End Effector Component Reloading System for Use with a Robotic System, published Jan. 10, 2013, the disclosure of which is incorporated by reference herein; U.S. Pub. No. 2012/0199630, entitled "Robotically-Controlled Surgical Instrument with Force-Feedback Capabilities," published Aug. 9, 2012, the disclosure of which is incorporated by reference herein; U.S. Pub. No. 2012/0132450, entitled "Shiftable Drive Interface for Robotically-Controlled Surgical Tool," published May 31, 2012, (now U.S. Pat. No. 8,616,431, issued on Dec. 31, 2013), the disclosure of which is incorporated by reference herein; U.S. Pub. No. 2012/0199633, entitled "Surgical Stapling Instruments with Cam-Driven Staple Deployment Arrangements," published Aug. 9, 2012 (now U.S. Pat. No. 8,573,461, issued on Nov. 5, 2013), the disclosure of which is incorporated by reference herein; U.S. Pub. No. 2012/0199631, entitled "Robotically-Controlled Motorized Surgical End Effector System with Rotary Actuated Closure Systems Having Variable Actuation Speeds," published Aug. 9, 2012 (now U.S. Pat. No. 8,602,288 issued on Dec. 10, 2013), the disclosure of which is incorporated by reference herein; U.S. Pub. No. 2012/0199632, entitled "Robotically-Controlled Surgical Instrument with Selectively Articulatable End Effector," published Aug. 9, 2012, the disclosure of which is incorporated by reference herein; U.S. Pub. No. 2012/0203247, entitled "Robotically-Controlled Surgical End Effector System," published Aug. 9, 2012 (now U.S. Pat. No. 8,783,541 issued on Jul. 22, 2014), the disclosure of which is incorporated by reference herein; U.S. Pub. No. 2012/0211546, entitled "Drive Interface for Operably Coupling a Manipulatable Surgical Tool to a Robot," published Aug. 23, 2012 (now U.S. Pat. No. 8,479,969 issued on Jul. 9, 2013); U.S. Pub. No. 2012/0138660, entitled "Robotically-Controlled Cable-Based Surgical End Effectors," published Jun. 7, 2012 now U.S. Pat. No. 8,800,838 issued on Aug. 12, 2014), the disclosure of which is incorporated by reference herein; and/or U.S. Pub. No. 2012/0205421, entitled "Robotically-Controlled Surgical End Effector System with Rotary Actuated Closure Systems," published Aug. 16, 2012 (now U.S. Pat. No. 8,573,465 issued on Nov. 5, 2013), the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
   (a) a body;
   (b) a shaft extending from the body and defining a longitudinal axis; and
   (c) an end effector in communication with the shaft, wherein the end effector is operable to compress, staple, and cut tissue, wherein the end effector comprises:
      (i) an anvil, wherein the anvil is movable between an open position and a closed position, wherein the anvil has a distal tip, wherein the end effector further projects from the shaft along the longitudinal axis such that the longitudinal axis intersects the distal tip of the anvil when the anvil is in the closed position, and
      (ii) a cartridge having a distal end portion including an upper surface and a lower surface, wherein the upper surface and the lower surface taper distally toward the longitudinal axis, wherein the upper surface has a proximal surface portion and a distal surface portion and the longitudinal axis intersects the distal surface portion of the upper surface, wherein the cartridge defines a sight line extending along the lower surface of the distal end portion of the cartridge toward the anvil, wherein the lower surface is opposite to the anvil and neither parallel to nor perpendicular to the longitudinal axis, wherein the sight line intersects the longitudinal axis near the distal tip of the anvil when the anvil is in the closed position, wherein a segment of the sight line and a segment of the longitudinal axis define an angle θ, wherein the segment of the sight line is on a cartridge side of the longitudinal axis, wherein the segment of the longitudinal axis is distal to the sight line, wherein the angle θ is larger than 90.

2. The apparatus of claim 1, wherein the distal end portion of the cartridge has a triangular profile.

3. The apparatus of claim 1, wherein the anvil comprises a tapered distal end.

4. The apparatus of claim 1, wherein the distal tip of the anvil comprises a rounded tip, wherein an underside portion of the distal tip of the anvil is rounded.

5. The apparatus of claim 1, wherein the distal tip of the anvil comprises a ball tip.

6. The apparatus of claim 5, wherein the ball tip comprises a polished surface.

7. The apparatus of claim 1, wherein the anvil comprises a ball groove, wherein the upper surface of the distal end portion comprises a cartridge ball tip, wherein at least a portion of the cartridge ball tip is configured to fit in the ball groove.

8. The apparatus of claim 1, wherein the anvil defines an underside of the anvil, wherein the underside comprises a plurality of recesses.

9. The apparatus of claim 8, wherein each of the plurality of recesses are spaced apart in an equally spaced manner.

10. The apparatus of claim 1, wherein the anvil comprises a cap portion operable to cover at least a portion of the anvil.

11. The apparatus of claim 10, wherein the cap portion defines the distal tip of the anvil.

12. The apparatus of claim 10, wherein the anvil comprises an anvil body formed of a first material, wherein the cap portion is secured to the anvil body, wherein the cap portion is formed of a second material, wherein the second material has a contrasting color operable to provide visual distinction of the cap portion from the anvil body.

13. The apparatus of claim 1, wherein the anvil comprises an anvil body formed of a first material, wherein the distal tip of the anvil forms an opening, wherein a cap formed of a second material is anchored in the opening.

14. The apparatus of claim 1, wherein the cartridge defines a cartridge tip at the distal end of the cartridge, wherein the distal tip of the anvil extends distally beyond the cartridge tip.

15. An apparatus comprising:
   (a) a body;
   (b) a shaft extending from the body and defining a longitudinal axis; and
   (c) an end effector in communication with the shaft such that the end effector projects therefrom along the longitudinal axis, wherein the end effector is configured to compress and staple tissue, wherein the end effector comprises:
      (i) an anvil, wherein the anvil comprises has a proximal portion and a distal portion, wherein the proximal portion extends along a plane, wherein the distal portion does not extend along the plane, and
      (ii) a cartridge having a distal end portion including an upper surface and a lower surface, wherein the upper surface and the lower surface taper distally toward the longitudinal axis, wherein the upper surface has a proximal surface portion and a distal surface portion and the longitudinal axis intersects the distal surface portion of the upper surface, wherein the upper and lower surfaces of the cartridge extend toward each other at a location proximate to the distal portion of the anvil, wherein the distal portion of the anvil complements the upper surface of the cartridge.

16. The apparatus of claim 15, wherein the anvil comprises a distal tip, wherein the lower surface defines a sight line that extends to the distal tip.

17. The apparatus of claim 15, wherein the anvil comprises a plurality of recesses.

18. The apparatus of claim 15, wherein the anvil comprises an anvil ball tip, wherein the cartridge comprises a cartridge ball tip.

19. An apparatus comprising:
   (a) a body; and
   (b) an end effector in communication with the body, wherein the end effector defines a longitudinal axis, the end effector comprising:
      (i) an anvil defining a distal portion,
      (ii) a lower jaw, wherein the anvil is movable toward the lower jaw, wherein a distal portion of the lower jaw is positioned at an oblique angle relative to the longitudinal axis, and
      (iii) a cartridge removably received in the lower jaw, wherein the cartridge is operable to drive staples toward the anvil;
   wherein a distal most portion of one of the anvil or the cartridge has a protruding tip feature,
   wherein the distal portion of the other of the anvil or the cartridge has a recess feature complementing the protruding tip feature,
   wherein the protruding tip feature is configured to fit in the recess feature.

20. The apparatus of claim 1, wherein the upper surface of the distal end portion comprises a cartridge ball tip, and wherein the longitudinal axis extends through the cartridge ball tip.

* * * * *